United States Patent [19]

Witkamp et al.

[11] Patent Number: 4,921,954
[45] Date of Patent: May 1, 1990

[54] PROCESS FOR THE PREPARATION OF CEPHEM COMPOUNDS

[75] Inventors: Hendrik A. Witkamp, Pijnacker; Jan Verweij, Leiden; Jan J. DeKoning, Rijswijk; Herman H. Grootveld, Benthuizen; Everardus J. A. M. Leenderts, Rhoon, all of Netherlands

[73] Assignee: Gist-Brocades N.V., Delft, Netherlands

[21] Appl. No.: 216,877

[22] Filed: Jul. 8, 1988

[30] Foreign Application Priority Data

Jul. 10, 1987 [EP]  European Pat. Off. ........ 87201316.4

[51] Int. Cl.⁵ .................. C07D 501/04; A61K 31/545
[52] U.S. Cl. ..................... 540/222; 540/225; 540/226; 540/227; 540/221; 540/230
[58] Field of Search ............... 540/230, 225, 222, 221, 540/226, 227; 514/206

[56]  References Cited

FOREIGN PATENT DOCUMENTS 0137534  4/1985  European Pat. Off. .
2279754  7/1975  France .
88201437  2/1969  Luxembourg .

Primary Examiner—Nicholas S. Rizzo
Attorney, Agent, or Firm—Bierman & Muserlian

[57]  ABSTRACT

Process for the preparation of 7β-amino-3-substituted methyl-3-cephem-4-carboxylic acid derivatives, new intermediates comprising 7β-(cyclo)alkylideneammonio-3-halomethyl-3-cephem-4-carboxylic acid derivatives and 7β-amino/ammonio-3-bromomethyl-3-cephem-4-carboxylic acid derivatives and the processes for the preparation of these intermediates.

2 Claims, No Drawings

PROCESS FOR THE PREPARATION OF CEPHEM COMPOUNDS

The invention relates to a new process for the preparation of certain cephalosporins. More particularly, the invention relates to a one-pot process for the preparation of 3-substituted methyl-3-cephem-4-carboxylic acid derivatives.

European Patent Application No. 0137534 discloses a multi-step one-pot process for the preparation of 7β-amino-and 7β-acylamino-3-substituted methyl-3-cephem-4-carboxylic acid derivatives by a bromination of the 3-methyl group of a deacetoxycephalosporin 1β-oxide, replacement of the bromo atom in the 3-bromomethyl group by another substituent, deoxygenation of the sulphoxy group and removal of a 7β-acyl substituent to give a cephalosporin with the free 7β-amino group. In this process the introduction of new substituents leading to various important intermediates takes place halfway the process. This makes optimization necessary for every single intermediate.

It has surprisingly been found that new nucleophilic substituents can be easily introduced at the last stage of the process without the occurrence of any side-reaction, such as isomerisation of the double bond. This was unexpected because reactions of the cephalo-derivative in the deoxygenated form generally are more sluggish and may give rise to isomerisation in the cephem moiety.

Therefore, in accordance with the present invention a process is provided for the preparation of 3-substituted methyl-3-cephem-4-carboxylic acid derivatives of formula I

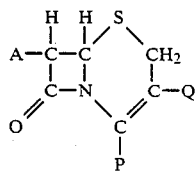

wherein
A is —NH$_2$,

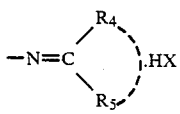

or —NH$_2$.HX,
P is —COOH; or —COO$\ominus$ when Q is —CH$_2\oplus$R$_2$,
Q is —CH$_2$R$_1$ and A is NH$_2$; or Q is CH$_2$X and A is —NH$_2$, NH$_2$. HX or

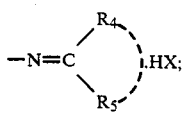

or Q is —CH$_2\oplus$R$_2$ and A is —NH$_2$; or Q is —CH$_2\oplus$R$_2$.X$\ominus$ and A is —NH$_2$ or —NH$_2$.HX,
R$_1$ is (lower)alkoxy, (lower)alkylthio, (lower)alkanoyloxy, (lower)alkanoylthio or S—R$_3$ where R$_3$ is an optionally substituted heterocyclic ring,
X is halogen or a mixture thereof when A is

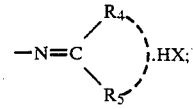

or X is bromo or chloro or a mixture thereof when A is —NH$_2$ or —NH$_2$. HX,
R$_2$ is a

group,
R$_4$ is alkyl, with up to 8 carbon atoms,
R$_5$ is alkyl, with up to 8 carbon atoms,
whereby R$_4$ and R$_5$ are the same or different or R$_4$, R$_5$ together with the carbon atom to which they are attached form cycloalkylidene with up to 8 carbon atoms; starting from 3-methyl-3-cephem-4-carboxylic acid 1β-oxide derivatives of formula II,

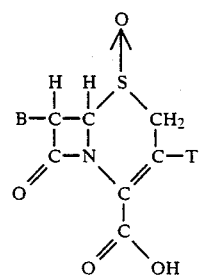

wherein
B is

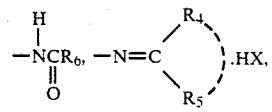

—NH$_2$ or —NH$_2$.HX,
T is —CH$_3$ when B is

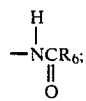

or T is —CH$_2$X where X is halogen or a mixture thereof when B is

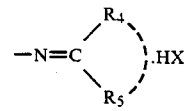

or X is bromo or chloro or a mixture thereof when B is —NH$_2$ or —NH$_2$. HX,
R$_4$ and R$_5$ are as defined above,
R$_6$ is an optionally substituted methyl group —CH$_2$R$_7$ which can be introduced by penicillin fermentation, and wherein R$_7$ is hydrogen, aryl, alkyl, cycloalkyl, alkenyl, aryloxy, alkyloxy, arylthio, alkylthio, or R$_6$ is an optionally substituted aryl group, by carrying out subsequently the following reactions preferably in the same reaction vessel without isolation of the intermediate products: when A is —NH$_2$, Q is —CH$_2$R$_1$, or CH$_2$⊕R$_2$ or —CH$_2$⊕R$_2$X⊖, and P, R$_{1-3}$ and X are as defined above, and B is

and T, R$_6$ and R$_7$ are as defined above:

(a) silylation of the carboxy group, optionally carried out in situ, (b) light-induced bromination of the 3-methyl group of a compound of formula II to give a compound with the 3-bromomethyl group, using a N-bromo-amide or a N-bromo-imide as brominating agent, (c) if necessary, replacement of any bromine introduced in step (b) in the methylene group adjacent to the sulphur atom in the dihydrothiazine ring by hydrogen by reaction with a trialkyl or triaryl phosphite, (d) deoxygenation of the sulphoxy group employing phosphorus pentachloride in the presence of an olefinic compound having at least one carbon-carbon double bond with no more than two hydrogen atoms attached thereto, and optionally in the presence of added or already present catalyst or —CH additive, (e) an imidechloride forming reaction splitting the 7β-acylamino substituent according to known procedures by adding sequentially N,N-dimethylaniline or other suitable tertiary amine and phosphorus pentachloride, (f) a reaction of the imidechloride with an alcohol such as isobutanol or 1,3-dihydroxypropane to form the corresponding iminoether and/or the 7-amino-cephem derivative, (f') optional addition of sodium iodide, (f'') optional formation of a 7β-(cyclo)alkylideneimino/ammonio derivative by adding a ketone and (g) introduction of the substituent R$_1$ or R$_2$ by replacement of the bromine in the 3-bromomethyl group, introduced in step (b), and if necessary, water for hydrolysis of the ammonio group; when A is

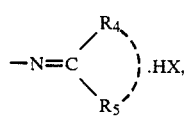

and P, Q, R$_{1-5}$ and X are as defined above, and B is

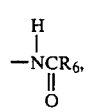

and T, R$_6$ and R$_7$ are as defined above:
by carrying out reactions a-f as described above, and adding a ketone R$_4$R$_5$CO;

when A is —NH$_2$ or —NH$_2$.HX, Q is —CH$_2$X and P and X are as defined above, and B is

and T, R$_6$ and R$_7$ are as defined above:
by carrying out reactions a-f as described above, and if necessary, adding water for hydrolysis of the ammoniogroup;

when A is

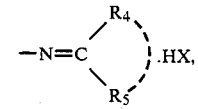

Q is —CH$_2$Br and P, X, and R$_4$ and R$_5$ are as defined above, and B is

and T, R$_6$ and R$_7$ are as defined above:
by carrying out reactions a-f as described above, and adding a ketone R$_4$R$_5$CO in the presence of an acid other than HCl;

when A is

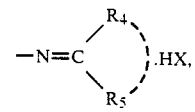

Q is —CH$_2$Cl and P, X, R$_4$ and R$_5$ are as defined above, and B is

and T, R$_6$ and R$_7$ are as defined above:
by carrying out reactions a-f as described above, and adding a ketone R$_4$R$_5$CO in the presence of hydrogen chloride or in the presence of a chloride providing agent together with a nitrogen containing base;

when A is —NH$_2$ or —NH$_2$.HX, Q is —CH$_2$R$_1$ or —CH$_2$⊕R$_2$ or —CH$_2$⊕R$_2$X⊖ and P, R$_1$ and X are as defined above, and B is

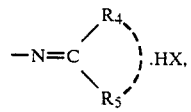

and T, R$_4$ and R$_5$ are as defined above:
introduction of the substituent R$_1$ or R$_2$ by replacement of halogen in the halomethyl group and, if necessary, water for hydrolysis of the ammoniogroup;

when A is

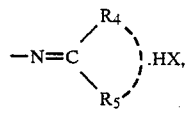

Q is —CH₂X, and P, X, R₄ and R₅ are as defined above, and
B is

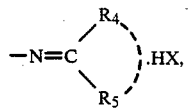

another one than being prepared or B is —NH₂.HX, and T, X, R₄ and R₅ are as defined above:
  addition of a suitable ketone R₄R₅CO, corresponding with B;
when A is —NH₂ or —NH₂.HX, Q is —CH₂X and P and X are as defined above, and
B is

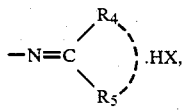

and T, X, R₄ and R₅ are as defined above: water for hydrolysis of the ammoniogroup.

For instance, compounds of formula I are prepared and isolated from compounds of formula II wherein
Q is —CH₂R₁,
R₁ is
  (1-sulfomethyl-tetrazol-5-yl)thio,
  (1-methyl-tetrazol-5-yl)thio,
  (1,2,3-triazol-5-yl)thio,
  (1-carboxymethyl-tetrazol-5-yl)thio,
  (1-(2-dimethylamino)ethyl-tetrazol-5-yl)thio,
  (5-methyl-1,3,4-thiadiazol-2-yl)thio,
and A, P and X are as defined above, and B is
and T, R₆ and R₇ are as defined above;
A is

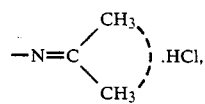

Q = —CH₂X where X is bromo or chloro, and P is as defined above, and B is

and T, R₆ and R₇ are as defined above;
A is —NH₂ or —NH₂.HCl, Q is —CH₂X where X is bromo or chloro or a mixture thereof, and P is as defined above, and
B is

and T, R₆ and R₇ are as defined above;
Q is —CH₂R₁ or —CH₂ ⊕R₂ or —CH₂ ⊕R₂X⊖ where
R₁ is (1,2,3-triazol-5-yl)thio, (1-methyl-tetrazol-5-yl)thio, (5-methyl-1,3,4-thiadiazol-2-yl)thio, (6-hydroxy-2-methyl-5-oxo-1,2,4-triazol-3-yl)-thio, (1,3,4-thiadiazol-5-yl)thio,
R₂ is (1-pyridinio), (quinuclidinio-1-ylio) (1-methyl-pyrrolidin-1-ylio) (cyclopenta[b]pyridin-1ylio),
and A, P and X are as defined above, and B is —NH₂, —NH₂.HX or

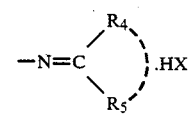

where R₄,R₅ is isopropylidene, cyclopentylidene or cyclohexylidene and T and X are as defined above;
A is

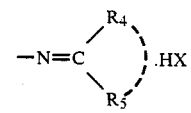

where
  R₄,R₅ is isopropylidene,
  R₄,R₅ is isobutylidene,
  R₄,R₅ is cyclopentylidene,
  R₄,R₅ is cyclohexylidene,
  R₄,R₅ is cycloheptylidene,
and P and X are as defined above, and B is

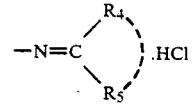

where R₄,R₅ is isopropylidene or cyclopentylidene, another one than being prepared, or B is —NH₂ or —NH₂. HX, and T and X are as defined above;
A is

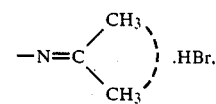

Q and P are as defined above, and
B is —NH₂ and T is as defined above;
A is —NH₂, Q and P are as defined above, and B is

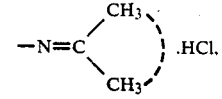

and T is as defined above.

The present invention also provides new halo-substituted cephalosporins of the general formula IC and salts and esters thereof

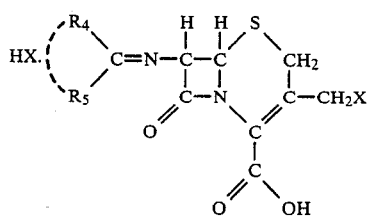

wherein
X is a halogen and $R_4$ and $R_5$ are defined as above; and new halo-substituted cephalosporins of the general formula ID and salts and esters thereof

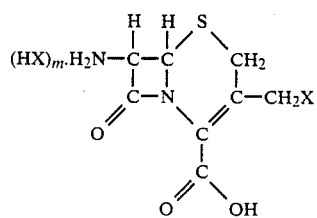

wherein
X is bromo or chloro and m is 0 or 1.

Suitable new intermediates are compounds with formula IC wherein
$R_4,R_5$ is isopropylidene,
$R_4,R_5$ is isobutylidene,
$R_4,R_5$ is cyclopentylidene,
$R_4,R_5$ is cyclohexylidene,
$R_4,R_5$ is cycloheptylidene, and
X is bromo or chloro;
and new intermediate with formula 1D wherein
HX is HCl and —$CH_2X$ is —$CH_2Br$.

The various aspects of the present invention are depicted in scheme I, wherein m is 0 or 1 and n is 0, 1 or 2.

All the reactions involving these new intermediates are carried out in inert organic solvents at −60° to +150° C., preferably at −40° to +100° C. With lower alkyl or (lower)alkyl in a compound, an alkyl group with up to 8 carbon atoms is meant. With $R_{n-n+m}$ is meant: $R_n$, $R_{n+1}$ ... $R_{n+m}$.

With "halogen or a mixture thereof" and "bromo or chloro or a mixture thereof", respectively, is meant that the compounds with formula I and II may be pure compounds regarding X or a mixture of compounds with different halogen atoms and bromo or chloro atoms, respectively.

According to an aspect of the present invention a process is provided for the preparation of 7β-amino-3-substituted methyl-3-cephem-4-carboxylic acid derivatives of formula I (depicted above) from 7β-acylamino-3-methyl-3-cephem-4-carboxylic acid 1β-oxide derivatives of formula II (depicted above).

The heterocyclic radical $R_3$ may be pyridine, pyrimidine, pyridazine, pyrroly, imidazole, pyrazole, isoxazole, isothiazole, thiazole, triazole, oxadiazole, thiadiazole, triazine, thiatriazole and tetrazole linked by a ring carbon atom to the sulphur atom, whereby optional substituents attached to a ring carbon atom of a heterocyclic ring include optionally substituted lower alkyl, cyano, chloro, di(lower)alkylamino, (lower)alkyloxy like methoxy, (lower)alkyloxycarbonyl, di(lower)alkylcarbamoyl, hydroxy, sulfo and carboxy, while ring nitrogen atoms of the heterocyclic thio group can have attached thereto an optionally substituted lower alkyl group, and optional substituents attached to the first or the second carbon atom of a lower alkyl group attached to a carbon or a nitrogen atom of a heterocyclic ring may include di(lower)alkylamino, chloro, cyano, methoxy, (lower)alkyloxycarbonyl, N,N-dimethylcarbamoyl, hydroxy, carboxy and sulfo.

The positively charged nitrogen group $R_2$ may be for instance a

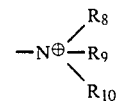

group wherein,
$R_8$ is alkyl, with up to 8 carbon atoms
$R_9$ is alkyl, with up to 8 carbon atoms
$R_{10}$ is alkyl, with up to 8 carbon atoms
whereby $R_8$, $R_9$ and $R_{10}$ are the same or different; or two of them form cycloalkyl with up to 8 carbon atoms and the third one is alkyl, with up to 8 carbon atoms, for instance $R_8,R_9$ together with the nitrogen atom form a pyrrolidine ring, $R_{10}$ is methyl; or $R_8$, $R_9$ and $R_{10}$ form with the nitrogen a heterocyclic ring as a 1-pyridinium or quinuclidinium group optionally having substituents attached to the heterocyclic ring.

It will be clear that the possibility of the introduction of a new substituent at the end of a sequence of reactions as described in this application will enlarge the flexibility of a manufacture plant and lower the costs of the products produced therein. Thus, an advantage of the present process is the introduction of the substituent in a late phase thereof so that the uniformity of the process will be longer maintained.

A further important advantage of this process is that there are no special demands relating to the form wherein the thiol compounds have to be added to the cephalosporin derivatives. Contrary to the process described in the above-mentioned EPA No. 0137534 or in the European patent specification No. 0045760 surprisingly it does not make difference whether the thiol compound is added as such, as thiolates (with or without crystal water) or as silyl derivative. The water optionally present does not cause any side-reaction.

Generally, yields are similar with the yields obtained according to the process described in EPA No. 0137534. Sometimes it may be preferable to add a ketone to the reaction mixture after having carried out the iminoether forming reaction in order to obtain ammonium compounds.

A preferred group of compounds which can be prepared according to the method of the invention is a group represented by formula IA

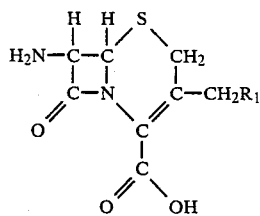

wherein R₁ is as defined above.

Another preferred group of compounds which can be prepared according to the method of the invention is a group represented by formula IB, IB' or IB''

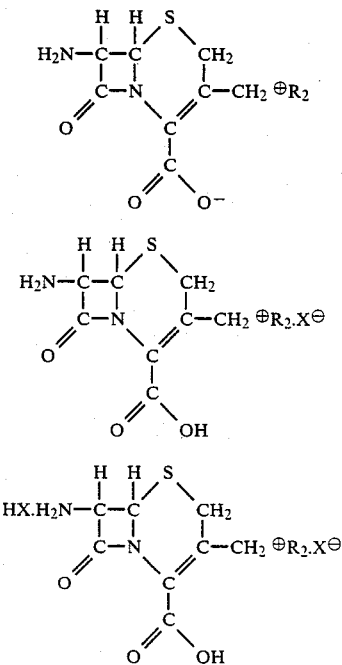

wherein R₂ is as defined above and X is bromo or chloro or a mixture thereof.

The invention also relates to new intermediates, viz. 7β-(cyclo)alkylideneammonio-3-halomethyl-3-cephem-4-carboxylic acid derivatives of the general formula IC (depicted above) and salts and esters thereof, wherein
X is halogen, and
R₄,R₅ are as defined above; and to 7β-amino/ammonio-3-bromomethyl-3-cephem-4-carboxylic acid and 7β-amino/ammonio-3-chloromethyl-3-cephem-4-carboxylic acid derivatives of the general formula ID (depicted above) and salts and esters thereof wherein
X is bromo or chloro, and
m is 0 or 1,
and to the isolation of these compounds from the reaction mixture.

A number of new cephalosporin derivatives formed in the course of the above-described process can be isolated. This concerns in the first place a mixture of 7β-(cyclo)alkylideneammonio-3-bromomethyl-3-cephem-4carboxylic acid and 7β-(cyclo)alkylideneammonio-3-chloromethyl-3-cephem-4-carboxylic acid derivatives. They can be isolated as a crystalline material after adding a ketone to the reaction mixture, simply by filtration. It is also possible to carry out the reaction in such a way that either the 3-bromo or 3-chloromethyl compound are formed. The 3-bromomethyl compound can be formed adding an acid other than hydrogen chloride before or simultaneously with the ketone. The 3-chloromethyl compound, for instance can be prepared by adding a sufficient amount of hydrogen chloride. Sofar in the literature only cefalosporanic acid derivatives with an aldimine substituent at the 7-position have been described for instance by W. A. Spitzer, T. Goodson, R. J. Smithey and I. G. Wright, J.C.Soc. Chem. Comm., 1338 (1972).

According to an aspect of the invention the proportion of both halogen compounds in 7β-(cyclo)alkylideneammonio-3-halomethyl-3-cephem-4-carboxylic acid derivatives can be influenced. Generally, more of the 3-bromomethyl compound seems to be formed in "acid" medium, while more of the chloromethyl compound is formed in a less "acid" medium. If, for instance, tetraethylammonium bromide is added to the reaction mixture, more of the chloromethyl compound is formed than without addition of this compound in spite of a larger amount of bromide present. Adding a chloride providing agent like a pentachloride in the presence of N,Ndimethylaniline does increase the yield of the chloromethyl compound. Generally, if an acid is added, a higher yield of the bromomethyl compound is obtained except in the case of an excess of hydrogen chloride. In that case the chloromethyl compound is formed in excess. These 7-(cyclo)alkylideneammonio-3-bromomethyl derivates are valuable intermediates for the preparation of many antibiotics, while the starting materials can be obtained in an economic way from penicillins.

Furthermore a mixture of 7β-ammonio-3-bromomethyl-3-cephem-4-carboxylic acid and 7β-ammonio-3-chloromethyl-3-cephem-4-carboxylic acid derivatives or the corresponding amino compounds (indicated throughout this text as 3-bromo/-chloromethyl) can be isolated. For this type of compounds intermolecular substitution could be expected, but this does not occur. In Spanish patent ES 461095 (no equivalents found) both the 3-bromomethyl and the 3-chloromethyl compound have been mentioned in the examples as starting compounds in a process to prepare 7β-amino-3-substituted methyl-3-cephem-4-carboxylic acid compounds in which the 7β-amino group temporarily has been protected with an aldehyde. In no way in this patent the source of these unknown and usually highly reactive starting compounds has been described, so it seems justified to ignore the only mention of these compounds in this patent.

According to another aspect of the invention 7β-amino-3-substituted methyl-3-cephem-4-carboxylic acid derivatives of formula I, with R₁ is as defined before, can be prepared directly from these new intermediate replacing the halogen atom by introduction of the desired substituent and, if necessary, by hydrolysis of the ammoniogroup. For instance, 7β-ammonio-4-carboxy-3[(1-pyridinio)-methyl]-3-cephem dichloride can be prepared in this way from 3-bromomethyl-4-carboxy-7β-isopropylideneammonio-3-cephem bromide in a nearly quantitative yield. In this way very interesting starting materials are available which easily can be converted in a simple one-step synthesis into 7β-amino-3-substituted methyl-3-cephem-4-carboxylic acid derivatives. An advantage of a process starting with 7β-(cyclo)alkylideneammonio-3-halomethyl-3-cephem-4-carboxylic acid derivatives, compared to the one described in the European Patent Application No. 0137534, is that virtually no deacetoxycephalosporin derivatives will be found in the end-products. The new intermediates (7β-(cyclo)alkylideneammonio-3-halomethyl-3-cephem-4-carboxylic acid derivatives and 7β-amino/ammonio-3-bromo-or chloromethyl-3-cephem-4-carboxylic acid) can also nearly quantitatively be converted in each other by addition of a suitable ketone or by hydrolysis of the ammoniogroup.

If during the one-pot process by addition of a ketone a mixture of the 3- bromomethyl and the 3-chloromethyl compound of a 7β-(cyclo)alkylideneammonio- derivative (indicated as 3-bromo/chloromethyl) has been formed, this mixture can be used to prepare the 3-substituted methyl derivatives. The same applies to the isolation of 7β-amino/ammonio-e-bromo-/chloromethyl-3-cephem-4-carboxylic acid derivatives from the one-pot process mixture. It is also possible to prepare the pure 3-halomethyl compound, for instance a pure 7β-amino/ammonio-3-bromomethyl-3-cephem-carboxylic acid derivative from a corresponding pure 7β-(cyclo)alkylideneammonio-3-bromomethyl derivative.

Both for the 7β-(cyclo)alkylideneammonio- as for the 7β-amino/ammonio-3-substituted methyl compound it is possible to convert the salt forming anion into another one.

The following non-limitative examples illustrate the invention. The preparation of the solution containing trimethylsilyl protected starting materials is described in the following "Preparation", which precedes the examples.

PREPARATION

Conversion of 7β-phenylacetamido-3-methyl-3-cephem-4-carboxylic acid 1β-oxide to a mixture containing trimethylsilyl 7β-phenylacetamido-3-bromomethyl-3-cephem-4-carboxylate 1β-oxide and a minor amount of trimethylsilyl 7β-phenylacetamido-2-bromo-3-bromomethyl-3-cephem-4-carboxylate 1β-oxide.

According to the process described in European Patent Application No. 0137534, a suspension of 113.0 g (316 mmoles in view of the actual content of 97.5% by weight) of 7β-phenylacetamido-3-methyl-3-cephem-4carboxylic acid 1β-oxide, of 11.0 g (110 mmoles) of succinimide, and of 0.3 g (1.64 mmoles) of saccharine in 2200 ml of dichloromethane was boiled without reflux in nitrogen atmosphere to remove traces of moisture by boiling off 200 ml of dichloromethane.

Subsequently 40 ml (188 mmoles) of hexamethyl disilazane were added. Upon stirring and passing over the surface of the reaction mixture nitrogen at a rate of 8 1 per hour to remove developing ammonia, boiling was continued at reflux. After about 3 hours the solution was clear and the generated gas no longer contained ammonia according to titration with acid.

Cooling down the solution to room temperature, 5 g (51 mmoles) of sulfaminic acid were added and thereafter upon stirring cooled to $-4°$ C. Subsequently the mixture was circulated by pumping from a cooled container through a double faced jacket enveloping a turned on fluorescence tube of 140 W with a peak at 350 nm. Operating under nitrogen atmosphere 40 g (225 mmoles) of N-bromo-succinimide were added at a temperature of $-4 \pm 2°$ C. After 5 minutes a second portion of 40 g of N-bromo-succinimide was introduced, whereupon irradiation was continued for about 65 minutes. The resulting solution weighed 2870 g, and contained according to HPLC-assay 0.070 mmol/g of trimethylsilyl 7β-phenylacetamido-3-bromomethyl-3-cephem-4-carboxylate 1β-oxide, which corresponds to a direct yield of 63.5%. Besides a relatively much smaller amount of trimethylsilyl 7β-phenyl-acetamido-2-bromo-3-bromomethyl-3-cephem-4-carboxylate 1β-oxide was present. In the subsequent examples this by-product was reduced in situ to trimethylsilyl 7β-phenylacetamido-3-bromomethyl-3-cephem-4-carboxylate 1β-oxide by the action of a trisubstituted phosphite, after which the content of this intermediate was again determined by HPLC-assay.

If such solutions containing the mixture of the monobromide and the dibromide are submitted to selective monodebromination directly after their preparation, the yield of the monobromide after debromination of the dibromide may be in the order of 70%. In the examples however, stock-solutions were employed normally so that the total content of the monobromide after debromination usually was in the order of 60% with respect to the initially used amount of 7β-phenylacetamido-3-methyl-3-cephem-4-carboxylic acid 1β-oxide, this being the consequence of storing the stock-solution for several days at about $-25°$ C.

EXAMPLE I

Preparation of the monosodium salt of 7β-amino-3-[[(1-sulfomethyl-tetrazol-5-yl)thio]methyl]-3-cephem-4carboxylic acid from 7β-phenylacetamido-3-methyl-3-cephem-4-carboxylic acid 1β-oxide.

(a) In the usual fashion, as described in European patent application No. 0137534, 2920 g of a solution in dichloromethane containing 173.2 mmoles of trimethylsilyl 7bβ-phenylacetamido-3-bromomethyl-3-cephem-4-carboxylate 1β-oxide and 40 mmoles of trimethylsilyl 7β-phenylacetamido-2-bromo-3-bromomethyl-3-cephem-4-carboxylate 1β-oxide was prepared by catalyzed hexamethyldisilazane silylation of 113 g (316 mmoles) of 7β-phenylacetamido-3-methyl-3-cephem-4-carboxylic acid 1β-oxide followed by light-induced bromination with N-bromo-succinimide in situ.

Continuously applying anhydrous conditions the solution obtained was treated in situ with 31.4 ml (116 mmoles) of tributyl phosphite during 15 minutes at $-18 \pm 3°$ C., followed by cooling to $-58°$ C. 31.6 ml (242 mmoles) of ciscyclooctene, 4.35 ml (34.3 mmoles) of N,N-dimethylaniline, 6.5 ml (84.3 mmoles) of N,N-dimethylformamide and 63.1 g (303 mmoles) of phosphorus pentachloride were added sequentially in situ, causing a rise in temperature to $-47°$ C. After 30 minutes stirring at $-47°$ C., 64.1 ml (513.5 mmoles) of N,N-dimethylaniline and 63.1 g (303 mmoles) of phosphorus pentachloride were introduced, followed by 70 minutes stirring at $-48°$ C. Subsequently 210 ml (226 mmoles) of isobutanol were added at $-60°$ C. followed by 2 hours stirring at about $-45°$ C., resulting in a mixture of 7β-ammonio-3-bromomethyl-3-cephem-4-carboxylic acid chloride and corresponding iminoethers of the 3-bromomethyl and/or 3-chloromethyl compounds.

(b) To the well stirred solution obtained as described hereinabove was added in 3 minutes a solution of 95 g (90.5%, 358 mmoles) of the disodium salt of 1-sulfomethyl-tetrazol-5-yl-thiol in 400 ml of water, whereby a temperature of $-13°$ C. was attained. The resulting mixture was stirred additionally for 22 minutes at −15° C. to −8° C., whereupon 65 ml of 25% sodium hydroxide in water were introduced to raise the pH from about −0.85 to about −0.15 at 0° C. After standing for 25 minutes at 0° C. the layers were separated and the organic phase was extracted with 120 ml of water. After removal by filtration of a small amount of precipitate, the aqueous layers combined were washed with 200 ml of dichloromethane and thereafter treated sequentially with 5 g (26 mmoles) of sodium metabisulphite, 950 ml of methanol and 208.5 ml of 25% sodium hydroxide in water to give pH 4.05. The resulting solution was left standing for about 16 hours at 3° C., whereupon the precipitated crystalline product was collected by filtration, followed by washings with 75 ml of a 3:2 mixture of methanol and water, and with acetone, respectively. After drying in vacuo at 45° C., 75.98 g of a monosodium salt of 7β-amino-3[[(1-sulfomethyl-tetrazol-5-yl)thio]methyl]-3-cephem-4-carboxylic acid were obtained in the form of heavy small cream-coloured crystals. According to HPLC-assay the purity of the isolated product was 82% by weight, from which it is calculated that the actual overall yield starting from 7β-phenylacetamido-3-methyl-3-cephem-4-carboxylic acid 1β-oxide was 46%. This product could be purified as follows: It was mixed with 335 ml of water in a 1.5 l beaker glass, followed by dissolution by means of adding 46.7 ml of 4N sodium hydroxide to give pH 8. While stirring, 4 g of sodium metabisulphite, 30 g of activated carbon and 650 ml of methanol were added, whereupon the pH was readjusted to 8 by addition of 2.8 ml of 4N hydrochloric acid. The mixture was filtered through a Seitz filter and the filter cake was washed with a mixture of 135 ml of methanol and 80 ml of water. The filtrates combined were diluted with 325 ml of methanol. While stirring, 41.5 ml of 4N hydrochloric acid were introduced slowly to give pH 4.0. The mixture was left standing for 16 hours at 3° C., whereafter the precipitated crystalline product was washed with 75 ml of 60% methanol and acetone. After drying in vacuo the yield was 64.49 g. As according to HPLC assay the purity was 87.5% by weight, the actual overall yield now amounted to about 41.5%.

IR (KBr-disc, values in cm$^{-1}$): 1800, 1615, 1530, 1405, 1340, 1220, 1040, 995 and 590.

PMR (D$_2$O+NaHCO$_3$, δ-values in ppm, 60 Mc, int. ref. 2,2-dimethylsilapentane-5-sulphonate): 3.21, 3.51, 3.64 and 3.93 (AB-q, J=18 Hz, 2H); 3.95, 4.18, 4.32 and 4.54 (AB-q, J=13.5 Hz, 2H); 4.71 (d, J=4.5 Hz, 1H); 4.99 (d, J=4.5 Hz, 1H); 5.51 (s, 2H).

EXAMPLE II

Preparation of
7β-amino-3-[[(1,2,3-triazol-5-yl)thio]methyl]3-cephem-4-carboxylic acid from
7β-phenylacetamido-3-methyl-3-cephem-4-carboxylic acid 1β-oxide.

(a) According to the method described in Example Ia, 415.4 g of a dichloromethane solution containing trimethylsilyl 7β-phenylacetamido-3-bromomethyl-3-cephem-4-carboxylate 1β-oxide and trimethylsilyl 7β-phenylacetamido-2-bromo-3-bromomethyl-3-cephem-4-carboxylate 1β- oxide (prepared from 44.73 mmoles of 7β-phenylacetamido-3-methyl-3-cephem-4-carboxylic acid 1β-oxide) were first treated with 4.44 ml (16.4 mmoles) of tributyl phosphite during 15 minutes at −15° C., resulting in a content of 29.43 mmoles of trimethylsilyl 7β-phenylacetamido-3-bromomethyl-3-cephem-4-carboxylate 1β-oxide according to HPLC assay. Thereafter the mixture was submitted in situ to sulphoxide reduction using 5.85 ml (44.9 mmoles) of cis-cyclooctene, 0.62 ml (8 mmoles) of N,N-dimethylformamide and 9.4 g (45.2 mmoles) of phosphorus pentachloride during 30 minutes at about −45° C., subsequently treated with 9.82 ml (77.5 mmoles) of N,N-dimethylaniline and 8.4 g (40.2 mmoles) of phosphorus pentachloride during 40 minutes at about −45° C., and finally subjected to treatment with 30 ml (323 mmoles) of isobutanol during 60 minutes at −40° C. to −35° C.

(b) To the well stirred solution of 7β-ammonio-3-bromomethyl-3-cephem-4-carboxylic acid chloride obtained as described hereinabove was added at fast rate a solution of 11.0 g (46.8 mmoles) of the pentahydrate of the disodium salt of 1,2,3-triazol-5-yl-thiol in 60 ml of water, resulting in a mixture of −10° C. After 60 minutes additional stirring at −10° C., the aqueous phase was separated from the organic phase, which organic phase was extracted with 20 ml of water. The water-layers combined were first washed with 50 ml of dichloromethane, whereupon 0.5 g of sodium metabisulphite and 125 ml of methanol were added. By slow addition of 16.7 ml of 25% sodium hydroxide in water the pH was raised from 0.25 to 4.0 at about 10° C. This resulted in an amorphous precipitate, which was collected by filtration and washed with 25 ml of 60% methanol and with acetone, respectively. After drying in vacuo at 45° C. the cream-coloured 7β-amino-3-[[(1,2,3-triazol-5-yl)thio]methyl]-3-cephem-4-carboxylic acid herewith obtained weighed 8.04 g. As according to HPLC assay the purity of the product was 89% by weight, the actual overall yield based on the initially used amount of 7β-phenylacetamido-3-methyl-3-cephem-4-carboxylic acid 1β-oxide was 51%.

IR (KBr-disc, values in cm$^{-1}$): 1810, 1620, 1540, 1410, 1345, 1290, 1230, 1150, 1115, 1060, 1000, 800 and 790.

PMR (DCOOD, δ-values in ppm, 360 Mc, int. ref. TMS): 3.84 and 3.92 (AB-q, 2H; J=18 Hz); 4.28 (s, 2H); 5.47 (d, 1H; J=4.5 Hz); 5.50 (d, 1H; J=4.5 Hz); 8.36 (s, 1H).

EXAMPLE III

Preparation of
7β-amino-3-[[1-carboxymethyl-tetrazol-5-yl)thio]-methyl]-3-cephem-4-carboxylic acid from
7β-phenylacetamido-3-bromomethyl-3-cephem-4-carboxylic acid 1β-oxide.

(a) A process was carried out described in Example Ia. Silylation, bromination and debromination in one pot applied on the starting material 7β-phenylacetamido-3-methyl-3-cephem-4-carboxylic acid 1β-oxide (43.2 mmoles) afforded 325 ml of a solution in dichloromethane, containing 26.6 mmoles of trimethylsilyl 7β-phenylacetamido-3-bromomethyl-3-cephem-4-carboxylate 1β-oxide according to HPLC-assay. Then 5.2 ml (40 mmoles) of cis-cyclooctene, 0.71 ml of N,N-dimethylaniline, 1.35 ml of N,N-dimethylformamide, and 9.9 g (47.5 mmoles) of phosphorus pentachloride were added at −45° C., followed by 30 minutes additional stirring at −45° C. 10.6 ml (83.6 mmoles) of N,N-dimethylaniline and 9.9 g (47.5 mmoles) of phosphorus pentachloride were further introduced, whereafter the mixture was stirred again for 30 minutes at the same temperature. Addition of 31.5 ml of isobutanol and 60 minutes additional stirring were carried out at −35° C.

(b) To the solution of crude 7β-ammonio-3-bromomethyl-3-cephem-4-carboxylic acid chloride thus prepared were added 10.6 g (52 mmoles) of the disodium salt of 1-carboxymethyl-tetrazol-5-yl-thiol. The temperature of the well stirred mixture was raised to 0° C., followed by 60 minutes stirring at 0° C. After introduction of 50 ml of cold water and 15 minutes stirring at 0° C., the organic phase was separated from the aqueous phase. The organic phase was two times extracted with 40 ml of cold water and was thereafter discarded. The water-layers combined were washed with dichloromethane, and thereafter diluted with 300 ml of cold methanol. After slow addition of 4N sodium hydroxide to give pH 3.6 the preparation was left standing overnight at 0° C. The precipitate formed was collected by filtration, washed with a cold 1:1 mixture of methanol and water and with acetone, respectively, and thereafter dried in vacuo over phosphorus pentaoxide. Isolated were 7.5 g of a crude product which apart from impurities contained the desired compound for about 75% as the amino dicarboxylic acid and 25% as a monosodium salt thereof, which was revealed by titration with sodium hydroxide on a small sample. According to PMR-assay with the help of a weighed amount of an internal reference the crude product contained 16.53 mmoles of 7β-amino-3-[[(1-carboxymethyltetrazol-5-yl)thio]methyl]-3-cephem-4-carboxylic acid/carboxylate (a purity of 87% by weight) corresponding with an overall actual yield of 38.6%, as calculated from the amount of 7β-phenylacetamido-3-methyl-3-cephem-4-carboxylic acid 1β-oxide.

(c) The title compound devoid of remaining monosodium salt was obtained in about 34% overall yield and with a purity of 95.6% by weight according to PMR-assay by dissolution of the crude product in a minimal volume of water with the help of 4N hydrochloric acid to pH 1.4, dilution with three parts of methanol, filtration and addition of 4N sodium hydroxide to pH 2.6. The precipitate was collected by filtration, washed with a small volume of a cold 1:1 mixture of methanol and water and with acetone, and dried in vacuo to constant weight.

IR (KBr-disc, values in $cm^{-1}$): 1820, 1635, 1550, 1370, 1130, 1080.

PMR ($DCO_2D$, δ-values in ppm, 250 Mc, int. ref. TMS): 3.83, 3.90, 3.90, 3.97 (AB-q, J=18 Hz, 2H); 4.50, 4.55, 4.64, 4.69 (AB-q, J=14 Hz, 2H); 5.43, 5.45, 5.47, 5.49 (AB-q, J about 5 Hz, 2H); 5.50 (s, 2H).

EXAMPLE IV

Preparation of 7β-amino-3-[[(1-(2-dimethylamino)ethyltetrazol-5-yl)thio]methyl]-3-cephem-4-carboxylic acid from a solution of crude 7β-phenylacetamido-3-bromomethyl-3-cephem-4-carboxylic acid 1β-oxide.

(a) A process was carried out as described in Example Ia. Silylation, bromination and debromination in one pot applied on the starting material 7β-phenylacetamido-3-methyl-3-cephem-4-carboxylic acid 1β-oxide (33.1 mmoles) afforded 260 ml of a solution in dichloromethane, containing 19.9 mmoles of trimethylsilyl 7β-phenylacetamido-3-bromomethyl-3-cephem-4-carboxylate 1β-oxide according to HPLC-assay. At −55° C. were added 3.80 ml (29.2 mmoles) of cis-cyclooctene and 7.66 g (36.8 mmoles) of phosphorus pentachloride, followed by 30 minutes stirring at −45° C. Then 7.62 ml (60.1 mmoles) of N,N-dimethylaniline and 7.66 g (36.8 mmoles) of phosphorus pentachloride were introduced at −45° C. After 30 minutes stirring at the same temperature 27 ml of isobutanol were added at −35° C., whereupon the mixture was stirred for 60 minutes at −35° C.

(b) To the well stirred solution obtained as described hereinabove were added 6.37 g (36.8 mmoles) of pulverized 1-(2-dimethylamino)ethyl-tetrazol-5-yl-thiol followed by stirring for 60 minutes at −10° C. and for 30 minutes at 0° C. Stirring was continued during 10 minutes after dilution with 100 ml of cold water, whereupon the aqueous phase was separated from the organic phase which was extracted twice with 50 ml of cold water. The aqueous layers combined were washed with dichloromethane, and thereafter stirred with activated carbon which was removed by filtration. Triethylamine was added to the filtrate to give pH 3.2, whereupon the solution was concentrated azeotropically in vacuo with n-butanol to give a volume of about 100 ml. Ethanol was added slowly to achieve complete precipitation. While stirring the preparation was kept at 0° C. during 45 minutes, whereupon the precipitate was collected by filtration, followed by washings with 70% ethanol, 96% ethanol and acetone, respectively. After drying in vacuo the yield of 7β-amino-3-[[(1-(2-dimethylamino)ethyl-tetrazol-5-yl)thio]methyl]-3-cephem-4-carboxylic acid chloride was 5.4 g. As indicated by quantitative PMR-assay on a solution of weighed amounts of the product and of a reference compound, the purity was 88% by weight. Calculating from the initially employed amount of 7β-phenylacetamido-3-methyl-3-cephem-4-carboxylic acid 1β-oxide the actual overall yield was 35.2%.

PMR ($D_2O$, δ-values in ppm, 60 Mc, int. ref. 2,2-dimethylsilapentane-5sulphonate): 3.07 (s, 6H); 3.77, 3.86, 3.96 (t, J=6 Hz, 2H); 3.83 (s, 2H); 4.32 (s, 2H); 4.92, 5.02, 5.12, 5.21 (t, J=6 Hz, 2H); 5.12, 5.21 (d, J=5.2 Hz, 1H); 5.27, 5.35 (d, J=5.2 Hz, 1H).

IR (KBr-disc, values in $cm^{-1}$): 3360, 1802, 1618, 1530, 1410, 1345, 1285.

EXAMPLE V

Preparation of 7β-amino-3-[[(1-methyl-tetrazole-5-yl)thio]methyl]-3-cephem-4-carboxylic acid from 7β-phenylacetamido-3-methyl-3-cephem-4-carboxylate 1β-oxide In the usual fashion, as described in the European Patent Application No. 0137534, a suspension of 100 g (purity 97.5%; 280 mmoles) of 7β-phenylacetamido-3-methyl-3-cephem-4-carboxylic acid 1β-oxide in 2000 ml of dichloromethane was silylated with hexamethyl disilazane and subsequently brominated with N-bromosuccinimide giving 2855 g of a reaction mixture containing a mixture of trimethylsilyl 7β-phenylacetamido-3-bromomethyl-3-cephem-4-carboxylate 1β-oxide and trimethylsilyl 7β-phenylacetamido-2-bromo3-bromethyl-3-cephem-4carboxylate 1β-oxide. Continuous applying anhydrous conditions 248.8 g of this stock-solution were cooled down to −60° C. and treated in situ with 2.5 ml (9.2 mmoles) of tributyl phosphite for 45 minutes. According to HPLC analysis, the reaction mixture contained 14.89 mmoles of trimethylsilyl 7β-phenylacetamido-3-bromomethyl-3-cephem-4-carboxylate, which corresponds to a yield of 61%. 2.7 ml (20.7 mmoles) of cyclooctene, 0.3 ml (2.7 mmoles) of N,N-dimethyl aniline and 0.5 ml (6.8 mmoles) of N,N-dimethylformamide were then added in situ followed by 5 g (24.1 mmoles) of phosphorus pentachloride after 5 minutes. After stirring for another 40 minutes 5.1 ml (40.5 mmoles) of N,N-dimethylaniline and 5 g (24.1 mmoles) of phosphorus pentachloride were added. After stirring for 200 minutes at −50° C. a solution of 4.5 g (30 mmoles) of sodium iodide in 100 ml of methanol was added. The temperature was allowed to rise to −10° C. and stirring was continued for 105 minutes. After adding 4.36 g (37.5 mmoles) of 5-mercapto-1-methyl-tetrazole, stirring for 50 minutes, keeping the reaction mixture overnight and stirring for another 180 minutes, the reaction mixture was added dropwise to a chilled mixture of 130 ml of water, 20 ml of butyl acetate and 8.3 g of sodium bisulphite. Meanwhile the pH was kept at 8 with a 4N potassium hydroxide solution. After separating the layers and extracting the organic layer with 3.5 ml of water, the combined water layers were washed with 25 ml of butyl acetate and brought to pH 3.5 with a 4N hydrochloric acid solution. After maintaining the mixture at 2° C. for 16 hours, the precipitate was filtered off, washed subsequently with a 3:7 mixture of propanol-2 and water, a 1:1 mixture of acetone and water and acetone, respectively, and dried in vacuo, thus yielding 3.27 g of the title compound. According to HPLC essay the purity was 83% by weight. The mother liquor contained another 6% of the title compound. The isolated overall yield starting from 7β-phenylacetamido-3-methyl-3-cephem-4-carboxylic acid 1β-oxide amounted to 33%.

EXAMPLE VI

Preparation of
7β-amino-3-[[(5-methyl-1,3,4-thiadiazol-2-yl)thio]methyl]-3-cephem-4-carboxylic acid from
7β-phenylacetamido-3-methyl-3-cephem-4-carboxylic 1β-oxide 341.6 g of the stock solution obtained as described in example V, containing a mixture of trimethylsilyl 7β-phenylacetamido-3-bromomethyl-3-cephem-4-carboxylate 1β-oxide and trimethylsilyl 7β-phenylacetamido-2-bromo-3bromomethyl-3-cephem-4carboxylate 1β-oxide, were treated with 3.4 ml (12.4 mmoles) of tributyl phosphite for 45 minutes at −60° C. Next, the reduction of the sulphoxide was carried out with 3.7 ml (28.1 mmoles) of cyclooctene, 0.5 ml (3.7 mmoles) of N,N-dimethylaniline, 0.7 ml (9.2 mmoles) of N,N-dimethylformamide and 6.8 g (32.6 mmoles) of phosphorus pentachloride. After stirring for 40 minutes at −60° C. 7 ml (54.9 mmoles) of N,N-dimethylaniline and 6.8 g (32.6 mmoles) of phosphorus pentachloride were added and stirring was continued for 200 minutes at −50° C. After adding a solution of 6.1 g (40.6 mmoles) of sodium iodide in 100 ml of methanol, the temperature was allowed to rise to −10° C. and stirring was continued for 105 minutes. 6.7 g (50.8 mmoles) of 2-mercapto-5-methyl-1,3,4-thiadiazole were then added, after which the reaction mixture was stirred for one hour at −10° C. and kept overnight at 0° C. After adding 50 ml of water and stirring for 15 minutes at 0° C., the layers were separated and the organic layer extracted with another 50 ml of water. To the combined water layers 50 ml of isobutanol were added and the pH was adjusted to 7.9 with ammonia. After separating the layers and extracting the isobutanol layer with water, the pH of the combined water layers was adjusted to 3.5 with a 4N sulfuric acid solution. After keeping the reaction mixture for 20 hours in the refrigerator the precipitate was filtered off, washed with water and acetone and dried in vacuo, yielding 5.85 g of the title product. The purity according to HPLC was 86.6%. The overall yield amounted to 44%.

EXAMPLE VII

Preparation of
7β-amino-[[(1,2,3-triazol-5-yl)thio]methyl]-3-cephem-4-carboxylic acid from
7β-phenylacetamido-3-methyl-3-cephem-4-carboxylic acid 1β-oxide in the presence of acetone (a) According to the method described in Example Ia, 526.5 g of a dichloromethane solution containing trimethylsilyl 7β-phenylacetamido-3-bromomethyl-3-cephem-4carboxylate 1β-oxide and trimethylsilyl 7β-phenylacetamido-2-bromo-3-bromomethyl-3-cephem-4-carboxylate 1β-oxide were cooled down to −52° C. and treated with 5.25 ml (19.4 mmoles) of tributyl phosphite during 48 minutes at −50±2° C.

Thereafter the mixture was submitted in situ to sulphoxide reduction using 5.7 ml (43.7 mmoles) of ciscyclooctene, 0.75 ml (5.9 mmoles) of N,N-dimethylaniline, 1.1 ml (14.3 mmoles) of N,N-dimethylformamide and 10.6 g (50.9 mmoles) of phosphorus pentachloride during 30 minutes at about −45° C., subsequently treated with 10.9 ml (86.0 mmoles) of N,N-dimethylaniline and 10.6 g (50.9 mmoles) of phosphorus pentachloride during 4 hours and 5 minutes at about −50° C., and finally subjected to treatment with 40 ml (431 mmoles) of isobutanol and 225 ml (3.06 mol) of acetone. The obtained solution was stirred during one hour at −40° C. whereafter it was preserved during the night in the refrigerator at −28° C. The reaction mixture was stirred for another two hours at −25° C. Stirring a sample was taken which contained 3-bromo/chloromethyl-4-carboxy-7β-isopropylideneammonio-3-cephem chloride.

To the well stirred solution obtained as described hereinabove was added at fast rate a solution of 13.0 g (55.3 mmoles) of the dihydrate of the disodium salt of 1,2,3-triazol-5-yl-thiol in 70 ml of water, resulting in a mixture of −5° C. Because a separation of the organic and water layer could not be obtained the solution was evaporated to a volume of 230 ml at the rotavapor at low temperature (0° C.). To the concentrate obtained after about half an hour 100 ml of trichloromethane and 25 ml of H$_2$O were added whereafter the layers were separated. The water-layers combined were first washed with 10 ml of trichloromethane, whereupon 0.6 g of sodium metabisulphite and 150 ml of methanol were added. By slow addition of 25% sodium hydroxide in water under cooling the pH was raised from 0.3 to 1.7 at about 15° C. Then the pH was raised within 1.5 hour to pH 2.4 at room temperature where crystallization occurs. Finally the pH was brought at 3.93 within 10 minutes. There was 38 ml of 25% (7.95 N) sodium hydroxide used. After a night standing in the refrigerator the crystal was filtered and washed with 25 ml of 60% methanol and with acetone, respectively. After drying in vacuo at 40° C. the cream-coloured 7β-amino-3-[[(1,2,3-triazol-5-yl)thio]methyl]-3-cephem-4-carboxylic acid herewith obtained weighed 9.0625 g. As according to HPLC assay the purity of the product was 85.5% by weight, the actual overall yield based on the initially used amount of 7β-phenylacetamido-3-methyl-3-cephem-4carboxylic acid 1β-oxide was 48%. The structure was confirmed by spectroscopic means.

EXAMPLE VIII

Preparation of
3-bromomethyl-4-carboxy-7β-isopropylideneammonio-3-cephem bromide from a solution of
7β-phenylacetamido-3-methyl-3-cephem-4-carboxylic acid 1β-oxide (a) According to the method described in Example Ia, 390.65 g of a dichloromethane solution containing trimethylsilyl 7β-phenylacetamido-3-bromomethyl-3-cephem-4-carboxylate 1β-oxide and trimethylsily 7β-phenylacetamido-2-bromo-3-bromomethyl-3-cephem-4-carboxylate 1β-oxide were cooled down to −65° C. and treated with 3.85 ml (14.2 mmoles) of tributyl phosphite during 70 minutes at −60±2° C.

Thereafter the mixture was submitted in situ to sulphoxide reduction using 4.2 ml (32.2 mmoles) of ciscyclooctene, 0.5 ml (3.9 mmoles) of N,N-dimethylaniline, 0.8 ml (10.4 mmoles) of N,N-dimethylformamide and 7.65 g (36.7 mmoles) of phosphorus pentachloride during 65 minutes at about −66° C., subsequently treated with 4.8 ml (37.9 mmoles) of N,N-dimethylaniline and 7.65 g (36.7 mmoles) of phosphorus pentachloride during 2 hours and 15 minutes at about −66° C., and subjected to treatment with 28 ml (30.3 mmoles) of isobutanol. After 1 hour and 30 minutes stirring at about −65° C. the reaction mixture was finally subjected to treatment with 345 ml (4.7 mol) of acetone and 19 ml (166 mmoles) of a solution of HBr, 47%.

The crystal was filtered and washed with methylene chloride and with acetone. After drying in vacuo at 40° C. the white-pink coloured 3-bromomethyl-4-carboxy-7β-isopropylideneammonio-3-cephem bromide herewith obtained weighed 8.1387 g.

IR-spectrum (KBr-disc; values in cm$^{-1}$): 3420, 1790, 1692, 1650, 1610, 1512, 1397, 1347, 1215, 1180, 1091, 1059, 992, 820, 720, 697, 620.

NMR-spectrum (360 MHz; CF$_3$CO$_2$D; δ-values in ppm; int. ref. maleic acid; δ=6.35): 2.54 (s, 3H); 2.63 (s, 3H); 3.53, 3.58 (AB-q or d, 2H; J=17.3 Hz); 4.29, 4.33 (AB-q or d, 2H; J=10.7 Hz); 5.33 (d, 1H; J=4.5 Hz); 5.83 (d, 1H; J=4.5 Hz).

EXAMPLE IX

Preparation and isolation of 7β-ammonio -3-bromomethyl-4-carboxy-3-cephem chloride from 7β-phenylacetamido-3-methyl-3-cephem-4-carboxylic acid 1-β-oxide According to the process described in Example Ia, 28.91 mmoles of 7β-phenylacetamido-3-methyl-3-cephem-4-carboxylic acid 1β-oxide in dichloromethane were converted by silylation and bromination into 267.7 g of a reaction mixture, containing trimethylsily 7β-phenylacetamido-3-bromomethyl-3-cephem-4-carboxylate 1β-oxide and a minor amount of its 2-bromo derivative. The solution was in the usual way treated with 3.2 ml of tributyl phosphite to give a solution containing 17.63 mmoles of trimethylsilyl 7β-phenylacetamido-3-bromomethyl-3-cephem-4-carboxylate 1β-oxide.

The solution obtained was cooled down to −45° C. followed by the introduction of 3.88 ml (30 mmoles) of ciscyclooctene, 0.42 ml (3.3 mmoles) of N,N-dimethylaniline, 0.38 ml (5 mmoles) of N,N-dimethylformamide and 6 g (28.8 mmoles) of phosphorus pentachloride, respectively, whereafter the mixture was stirred for 30 minutes at −45° C.

6 ml (47.6 mmoles) of N,N-dimethylaniline and 6 g (28.8 mmoles) of phosphorus pentachloride were added at the same temperature. After additional stirring during 30 minutes 22 ml (238 mmoles) of isobutanol were added slowly, followed by 60 minutes stirring at −35° C.

To the resulting reddish brown solution were added 2.6 ml (31.9 mmoles) of pyridine and 4.1 ml (31.9 mmoles) of trimethylsilyl chloride, followed by 30 minutes stirring at −10° C. The preparation was stored for 2 hours at −25° C. resulting in the formation of a precipitate. The precipitate was collected by filtration and washed with dichloromethane. The product obtained was dissolved in a minimal volume of methanol at 0° C., followed by slow addition of 10 ml of cold 1N hydrochloric acid and 200 ml of isopropanol, respectively. The resulting solution was concentrated in vacuo to a small volume. The almost white crystalline product formed hereby was collected by filtration, sequentially washed with cold isopropanol and n-hexane. After drying in vacuo the yield was 2.64 g. By PMR-assay, using a solution in DCO$_2$D prepared from weighed amounts of isolated product and maleic acid, it was found that the isolated product was the hydrochloric salt of 7β-amino-3-bromomethyl-3-cephem-4-carboxylic acid in about 85% purity by weight. Therefore, the actual overall yield was about 24%.

PMR (DCO$_2$D, δ-values in ppm, 300 Mc, int. ref. TMS): 3.79, 3.85, 3.91 (AB-q, J=18 Hz, 2H); 4.68, 4.72, 4.75, 4.79 (AB-q, J=12 Hz, 2H); about 5.50 (unsharp q, 2H).

IR (KBr-disc, values in cm$^{-1}$): 1865, 1630, 1550, 1420, 1360, 1135, 1065, 1018.

In zwitter-ionic form 7β-amino-3-bromomethyl-3-cephem-4-carboxylic acid was also obtained, albeit in much less pure state, from not purified 7β-phenylacetamido-3-bromomethyl-4-carboxylic acid 1β-oxide by, sequentially, silylation with trimethylchlorosilane and N,N-dimethylaniline, sulphoxide reduction and imidechloride formation with phosphorus pentachloride and N,N-dimethylaniline (with or without partial substitution of N,N-dimethylaniline by ciscyclooctene), treatment with isobutanol and thereafter with a minimal volume of water, and finally isolation of the precipitated compound by addition of sodiumbicarbonate to pH 3.5.

IR (KBr-disc, values in cm$^{-1}$): 1860, 1620, 1540, 1410, 1350, 1125, 1060, 1015.

EXAMPLE X

Preparation of
3-bromomethyl-4-carboxy-7β-isopropylideneammonio-3-cephem chloride from a solution of
7β-phenylacetamido-3-methyl-3-cephem-4-carboxylic acid 1β-oxide under various reaction conditions (a) According to the process described in Example Ia, 287 mmoles of 7β-phenylacetamido-3-methyl-3-cephem-4carboxylic acid 1β-oxide in 2 1 dichloromethane were converted into a stock-solution containing trimethylsilyl 7β-phenylacetamido-3-bromomethyl-3-cephem-4-carboxylate 1β-oxide and a minor amount of trimethylsilyl 7β-phenylacetamido-2-bromo-3-bromomethyl-3-cephem-4-carboxylate 1β-oxide and brought to −30° C. 5.0 ml of tributyl phosphite was added to a fourth part by weight of this stock solution during 20 minutes at −25° C.−−30° C. to reduce the dibromide into the monobromide.

The solution obtained hereinabove was cooled down to −60° C., followed by the introduction of 1 ml of N,N-dimethylaniline, 1.5 ml of N,N-dimethylformamide, 7.5 ml of cis-cyclooctene and 15 g of phosphorus pentachloride, whereupon the mixture was stirred for 30 minutes at −55° C.-−60° C.

15 ml of N,N-dimethylaniline and 15 g of phosphorus pentachloride were added, followed by 120 minutes stirring at −50° C.-−55° C. Subsequently 52.5 ml of isobutanol were added, followed by 60 minutes stirring at −25° C.-−30° C.

(b) The solution of 7β-ammonio-3-bromomethyl-4-carboxy-3-cephem chloride was divided in seven parts by weight. To each part 90 ml of acetone, together with the additives indicated in the table A, were added and the temperature was raised to 20° C.-25° C., then cooled down to 5° C. and stored overnight in the refrigerator. The precipitate was collected by filtration, washed with dichloromethane and acetone and dried in vacuo to constant weight at 20° C.-25° C. The results have been mentioned in table A. The purity of the isolated material has been established by quantitative assay being 70%. The proportion 3-bromomethyl substituted compounds (Br) versus 3-chloromethyl substituted compounds (Cl) and the yield of 3-bromomethyl-4-carboxy-7β-isopropylideneammonio-3-cephem chloride, were given in each entry.

TABLE A

| | additive | proportion Br:Cl | yield (g) | yield Br (%) |
|---|---|---|---|---|
| 1. | — | 70:30 | 1.91 | 24.7 |
| 2. | 1 ml H$_2$O | 84:16 | 2.03 | 31.5 |
| 3. | 5 ml H$_2$SO$_4$, conc | 94:06 | 1.61 | 27.9 |
| 4. | 5 ml H$_3$PO$_4$, 85% | 85:15 | 1.85 | 29.1 |
| 5. | 5 ml HBr, 47% | 94:06 | 1.96 | 34.0 |
| 6. | 10 ml HBr, 47% | 94:06 | 2.03 | 35.3 |
| 7. | 15 ml HBr, 47% | 93:07 | 1.85 | 31.8 |

EXAMPLE XI

Preparation of 3-bromomethyl-4-carboxy-7β-isopropylideneammonio-3-cephem chloride from a solution of 7β-phenylacetamido-3-methyl-3-cephem-4-carboxylic acid 1β-oxide under various reaction conditions Exactly in the same way as described in example X 3-bromomethyl-4-carboxy-7β-isopropylideneammonio-3-cephem chloride was prepared except that the additives were introduced 15 minutes before the acetone. The results are given in table B.

TABLE B

| | additive | proportion Br:Cl | yield (g) | yield Br (%) |
|---|---|---|---|---|
| 1. | — | 49:51 | 2.33 | 21.1 |
| 2. | 1 ml H$_2$O | 76:24 | 2.24 | 31.5 |
| 3. | 5 ml H$_2$SO$_4$, conc | 91:09 | 2.19 | 36.8 |
| 4. | 5 ml H$_3$PO$_4$, conc | 80:20 | 2.22 | 32.8 |
| 5. | 5 ml HBr, 47% | 90:10 | 2.27 | 37.7 |
| 6. | 10 ml HBr, 47% | 89:11 | 2.23 | 36.7 |
| 7. | 15 ml HBr, 47% | 88:12 | 2.08 | 33.8 |

EXAMPLE XII

Preparation of 4-carboxy-3-chloromethyl-7β-isopropylideneammonio-3-cephem chloride from a solution of 7β-phenylacetamido-3-methyl-3-cephem-4-carboxylic acid 1β-oxide under various reaction conditions Exactly in the same way as described in example X 4-carboxy-3-chloromethyl-7β-isopropylideneammonio-3-cephem chloride was prepared. The results are given in table C.

TABLE C

| | additive | proportion Cl:Br | yield (g) | yield Cl (%) |
|---|---|---|---|---|
| 1. | — | 42:58 | 2.01 | 17.7 |
| 2. | 2.5 ml DMA* | 56:44 | 1.96 | 23.0 |
| 3. | 2.5 ml DMA* + 2.5 g PCl$_5$ | 58:42 | 2.02 | 24.6 |
| 4. | 2.5 ml PCl$_5$ | 43:57 | 1.96 | 17.7 |
| 5. | 15 ml HCl | 94:06 | 1.40 | 27.6 |

*DMA = N,N-dimethylaniline.

EXAMPLE XIII

Preparation of 7β-amino-3-[[(1-methyl-tetrazol-5-yl)thio]methyl]-3-cephem-4-carboxylic acid from 3-bromomethyl-4-carboxy-7β-isopropylideneammonio-3-cephem bromide 800 mg (79% purity; 1.53 mmoles) of 3-bromomethyl-4-carboxy-7β-isopropylideneammonio-3-cephem bromide were added portionwise over about 30 minutes to a stirred solution of 232 mg (2.0 mmoles) of 5-mercapto-1-methyl-tetrazole in 10 ml of a 1:1 mixture of propanol-2 and water at 25° C. After adjusting the pH to 2.6 with 3.3 ml of 1N sodium hydroxide solution, the reaction mixture was stirred for another 45 minutes. After centrifugation, washing with a 1:1 mixture of water and acetone and with acetone, and drying in vacuo at 45° C. 543 mg of the title compound were obtained (purity according to HPLC: 82%; yield 88%).

IR (KBr-disc; values in cm$^{-1}$): 1800, 1615, 1535, 1410, 1350, 1290, 1275, 1255, 1170, 1120, 1060, 1010, 800, 790.

PMR (DCOOD; δ-values in ppm, 360 Mc, int. ref. TMS): 3.92 (s, 2H); 4.18 (s, 3H); 4.54 (s, 2H); 5.46 (d, 1H; J=4.5 Hz); 5.48 (d, 1H; J=4.5 HZ).

EXAMPLE XIV

Preparation of 7β-amino-3-[[(1,3,4-thiadiazol-2-yl)thio]methyl]-3-cephem-4-carboxylic acid from 3-bromomethyl-4-carboxy-7β-isopropylideneammonio-3-cephem bromide 800 mg (79% purity; 1.53 mmoles) of 3-bromomethyl-4-carboxy-7β-isopropylidenammonio-3-cephem bromide were added portionwise over about two hours to a well stirred solution of 236 mg (2.0 mmoles) of 2-mercapto-1,3,4-thiadiazole in 10 ml of a 1:1 mixture of propanol-2 and water at room temperature, while the pH was kept at 2.5 with 1N sodium hydroxide solution. After stirring for another 30 minutes at pH 2.5 the product was isolated by centrifugation and washed with a 1:1 mixture of water and acetone and with acetone, dried in vacuo at 45° C., thus giving 586 mg of the title compound.

IR (KBr-disc; values in cm$^{-1}$): 1805, 1620, 1545, 1415, 1370, 1350, 1065 and 805.

PMR (CF$_3$COOD; δ-values in ppm, 360 Mc, int. ref. TMS): 3.60 (s, 2H); 4.43 and 4.58 (AB-q, 2H; J=14.0 Hz); 5.13 (s, 2H); 9.92 (s, 1H).

EXAMPLE XV

Preparation of 7β-amino-3-[[(1,2,3-triazol-5-yl)thio]methyl]-3-cephem-4-carboxylic acid from 3-bromomethyl-4-carboxy-7β-isopropylideneammonio-3-cephem bromide To a solution of 246 mg (2.0 mmoles) of the sodium salt of 1,2,3-triazol-5-yl-thiol in 3 ml of water 7 ml of acetone were added. After adjusting the pH to 1.7 with 0.5 ml of 1N HCl, 800 mg (purity 79%; 1.53 mmoles) of 3-bromomethyl-4-carboxy-7β-isopropylideneammonio-3-cephem bromide were added portionwise over about 85 minutes while the pH was kept at 1.8 with 1N NaOH. After stirring for another 25 minutes the pH was adjusted to 2.2. After centrifugation, washing with 7.5 ml of a 1:1 mixture of water and acetone and with acetone, and drying in vacuo at 45° C., 378 mg of the title compound was obtained (purity according to HPLC 78%; overall yield 61.5%). The structure was confirmed by spectroscopic means.

EXAMPLE XVI

Preparation of 7β-amino-3-[[(1,3,4-triazol-2-yl)thio]methyl]-3-cephem-4-carboxylic acid from 3-bromomethyl-4-carboxy-7β-isopropylideneammonio-3-cephem bromide 800 mg (purity: 79%; 1.53 mmoles) of 3-bromomethyl-4-carboxy-7β-isopropylideneammonio-3-cephem bromide were added to a solution of 265 mg (2.0 mmoles) of 2-mercapto-5-methyl-1,3,4-thiadiazole in 15 ml of a 1:1 mixture of acetone and water at room temperature. The reaction mixture was shaken in an ultrasonic bath for 5 minutes and after one hour for another 5 minutes, diluted with a few millilitres of acetone and centrifugated. After washing the precipitate with acetone and diethylether and drying in vacuo 500 mg of the title compound were obtained with a purity of 84%. The overall yield was 80%.

IR (KBr-disc; values in cm$^{-1}$): 1805, 1620, 1545, 1515, 1410, 1380, 1150, 1060, 800 and 790.

PMR (CF$_3$COOD; 360 Mc, int. ref. TMS; δ-values in ppm): 2.83 (s, 3H); 3.54 and 3.62 (AB-q, 2H; J=16.2 Hz); 4.37 and 4.55 (AB-q, 2H; J=13.8 Hz); 5.11 (d, 1H; J=4.5 Hz); 5.14 (d, 1H; J=4.5 Hz).

EXAMPLE XVII

Preparation of 7β-amino-3-[[(5-methyl-1,3,4-thiadiazol-2-yl)thio]methyl]-3cephem-4-carboxylic acid from 3-bromo/chloromethyl-4-carboxy-7β-cyclopentylideneammonio-3-cephem bromide According to the procedure of Example XVI 454 mg of 7β-amino-3-[[(2-methyl-1,3,4-thiadiazol-2yl)thio]methyl]-3-cephem-4-carboxylic acid were obtained by reaction of a mixture of 3-bromomethyl-4-carboxy-7β-cyclopentylideneammonio-3-cephem chloride and the corresponding chloromethyl compound (800 mg); purity: 66% bromo compound, 20% chloro compound; 1.69 mmoles) with 265 mg of 2-mercapto-5-methyl-1,3,4-thiadiazole. Purity 83%, yield 65%.

EXAMPLE XVIII

Preparation of 7β-amino-3-[[(5-methyl-1,3,4-thiadiazol-2-yl)thio]methyl]-3-cephem-4-carboxylic acid from 7β-amino-3-bromomethyl-3-cephem -4-carboxylic acid A solution of 1N-sodiumhydroxide (about 3.4 ml) was added to 60 mg (0.45 mmol) of 2-mercapto-5-methyl-1,3,4-thiadiazole in 2 ml water till the solution was clear at a pH of 7.5. 100 mg (0.34 mmol) of 7β-amino-3-bromomethyl-3-cephem-4-carboxylic acid were added portionwise. About 2.8 ml of a solution of 0.1N NaOH was necessary to maintain the pH at about 7.5. Then the pH of the solution was adjusted to 4 with 3.6 ml of a solution of 0.1N HCl. The precipitate formed was filtered and washed with water and acetone. After drying in vacuo 61 mg of 7β-amino-3-[[(5-methyl-1,3,4-thiadiazol-2-yl)thio]methyl]-3-cephem-4-carboxylic acid were obtained with a purity of 62.5%. The overall yield was 32.5%.

IR (KBr-disc, values in cm$^{-1}$): about 3410, 1800, 1620, about 1540, 1412, 1350, 1060.

EXAMPLE XIX

Preparation of 7β-amino-3-[[(6-hydroxy-2-methyl-5-oxo-1,2,4-triazol-3-yl)thio]methyl]-3-cephem-4-carboxylic acid from 3-bromomethyl-4-carboxy-7β-isopropylideneammonio-3-cephem bromide 800 mg (79% purity; 1.53 mmoles) of 3-bromomethyl-4-carboxy-7β-isopropylideneammonio-3-cephem bromide were added portionwise over 80 minutes to a stirred solution of 318 mg (2.0 mmoles) of 6-hydroxy-1-mercapto-2-methyl-5-oxo-1,2,4-triazole in 10 ml of a 1:1 mixture of acetone and water at room temperature, while the pH was kept at 1.95 with a 1N NaOH solution (3.2 ml). After stirring for another 15 minutes the crystalline product was separated by centrifugation, washed with a mixture of acetone and water, with acetone and dried in vacuo, thus yielding 626 mg of the title compound. Purity 92%; yield 100%.

IR (KBr-disc; values in cm$^{-1}$): 1795, 1640, 1615, 1585, 1410, 1345, 1290, 1220, 1100, 800 and 785.

PMR (D$_2$O+NaHCO$_3$; 360 Mc, int. ref. TMS; δ-values in ppm): 369 (s, 3H); 3.49 and 3.71 (AB-q, 2H; J=18 Hz); 4.09 and 4.40 (AB-q, 2H; J=13.3 Hz); 4.80 (d, 1H; J=5 Hz); 5.10 (d, 1H; J=5 Hz).

EXAMPLE XX

Preparation of 7β-amino-3-[[(6-hydroxy-2-methyl-5-oxo-1,2,4-triazol-3-yl)thio]methyl]-3-cephem-4-carboxylic acid from 3-bromo/chloromethyl-4-carboxy-7β-cyclohexylideneammonio-3-cephem chloride According to the procedure of Example XVI 703 mg of 7β-amino-3-[[(6-hydroxy-2-methyl-5-oxo-1,2,4-triazol-3-yl)thio]methyl]-3-cephem-4-carboxylic acid were obtained starting from a mixture of 3-bromomethyl-4-carboxy-7β-cyclohexylideneammonio-3-cephem chloride and the corresponding 3-chloromethyl compound (1.3 g; purity: 69% bromo compound, 8.4% chloro compound; 2.76 mmoles) and 6-hydroxy-1-mercapto-2-methyl-5-oxo-1,2,4-triazole in 16 ml of a 1:1 mixture of acetone and water. The reaction temperature was 40° C. The purity of the final product was 92.5%. The yield was 64%.

EXAMPLE XXI

Preparation of
7β-ammonio-4-carboxy-3-[(1-pyridinio)-methyl]3-cephem dichloride from
3-bromomethyl-4-carboxy-7β-isopropylideneammonio-3-cephem bromide A mixture of 4.63 g (purity 85%; 9.5 mmoles) of 3-bromomethyl-4-carboxy-7β-isopropylideneammonio-3-cephem bromide, 50 ml of acetonitrile, 50 ml of acetone and 10 ml (40 mmoles) of N,O-bis(trimethylsilyl)acetamide was stirred under nitrogen at room temperature for 15 minutes and for 30 minutes at 0° C. After adding 10 ml (124 mmoles) of pyridine and stirring for 3 hours at 0° C. a clear orange solution was obtained. After pouring out the reaction mixture into a mixture of 5 ml of water, 10 ml of isopropanol and 5 ml of toluene, the solvents were evaporated. The residual solid was dissolved in 35 ml of a 1N hydrochloric acid solution at 0° C. After adding slowly 195 ml of isopropanol and stirring overnight at 0° C., the precipitate formed was centrifugated, washed with isopropanol and diethylether and dried in vacuo, yielding 3.55 g of the title compound. The yield was 92%.

IR (KBr-disc; values in cm$^{-1}$): 1795, 1610, 1487, 1395, 1335, 1280, 1240, 1150, 1050, 800, 770 and 680.

PMR (360 MHz; D$_2$O; δ-values in ppm): 3.40 and 3.77 (2xd, 2H; J=18 Hz); 5.26 (d, 1H; J=4.8 Hz); 5.35 (d, 1H; J=4.8 Hz); 5.45 and 5.64 (2xd, 2H; J=14.4 Hz); 8.16 (t, 2H; J about 6 Hz); 8.64 (t, 1H; J about 6 Hz); 9.00 (d, 2H; J about 6 Hz).

EXAMPLE XXII

Preparation of
7β-ammonio-4-carboxy-3-[(1-pyridinio)methyl]-3-cephem dichloride from
3-bromomethyl-4-carboxy-7β-isopropylideneammonio-3-cephem bromide A mixture of 463 mg (purity 85%, 0.95 mmole) of 3-bromomethyl-4-carboxy-7β-isopropylideneammonio-3-cephem bromide, 5 ml of acetone, 5 ml of acetonitrile and 1.1 ml (4 mmoles) of N,O-bis(trimethylsilyl)trifluoroacetamide was stirred under nitrogen for 30 minutes at 0° C. After addition of 1 ml of pyridine and stirring for three and a half hour the conversion into the title product was quantitative according to HPLC-analysis.

2 ml of water, 2 ml of isopropanol and 2 ml of toluene was added, the mixture was concentrated in vacuo to dryness and the remaining residue in 3.5 ml of a 1N hydrochloric acid solution. After adding slowly 20 ml of isopropanol and stirring for one and a half hour the mixture was centrifugated. Washing the precipitate with isopropanol and ether and drying in vacuo gave 364 mg of the title product with a purity of 93%. The yield was 98%.

EXAMPLE XXIII

Preparation of
7β-ammonio-4-carboxy-3-[(1-methylpyrrolidin-1-ylio)-methyl]-3-cephem dichloride from
3-bromomethyl-4-carboxy-7β-isopropylideneammonio-3-cephem bromide 463 mg (purity 85%, 0.95 mmole) of 3-bromomethyl-4-carboxy-7β-isopropylideneammonio-3-cephem bromide was silylated in a mixture of 5 ml of acetone and 5 ml of acetonitrile with 2 ml (8 mmoles) of N,O-bis(trimethylsilyl)acetamide under nitrogen at room temperature for 15 minutes. After cooling down and stirring for another 30 minutes a 0° C., a mixture of 0.24 ml (2.3 mmoles) of N-methylpyrrolidine, 20 ml of acetone and 20 ml of acetonitrile was added dropwise over a period of 60 minutes and stirring was continued at 0° C.

After addition of 1.5 ml of a 1N hydrochloric acid solution, 5 ml of isopropanol and 5 ml of toluene, the reaction mixture was concentrated in vacuo. Then 2.5 ml of a 1N hydrochloric acid solution and 30 ml of isopropanol was added and the mixture was concentrated to a volume of 20 ml and stored at 0° C. The crystalline precipitate formed was obtained by centrifugation. Washing and drying in vacuo gave 313 mg of the title compound with a purity of 72%. The yield was 64%.

IR (KBr-disc, values in cm$^{-1}$): 1790, 1640, 1620, 1600, 1400, 1345, 1290, 1145, 1065, 925 and 800.

PMR (360 MHz; D$_2$O; δ-values in ppm): 2.25 (m, 4 Hz); 3.01 (s, 3H); 3.57 (m, 4 Hz); 3.62 and 3.98 (2xd, 2H; J=18 Hz); 4.11 and 4.75 (2xd, 2H; J=13.2 Hz); 5.23 (d, 1H; J=4.5 Hz); 5.44 (d, 1H; J=4.5 Hz).

EXAMPLE XXIV

Preparation of
7β-ammonio-4-carboxylate-3-[(cyclopenta[b]pyridin-1-ylio)methyl]-3-cephem bromide from
3-bromomethyl-4-carboxy-7β-isohexylideneammonio-3-cephem bromide.

A mixture of 510 mg (purity 85%, 0.95 mmole) of 3-bromomethyl-4-carboxy-7β-cyclohexylideneammonio-3-cephem bromide, 5 ml of methylene chloride and 2 ml (8 mmoles) of N,O-bis(trimethylsilyl)acetamide was stirred for 15 minutes at room temperature and for 30 minutes at 0° C. Then with continuous stirring 0.28 ml of 2,3-cyclopenta[b]pyridine in 5 ml of methylene chloride was added during 10 minutes at 0° C. and stirring was continued for another 3 hours, the temperature for the last 30 minutes being 20° C. After concentrating the reaction mixture in vacuo and dissolving the residue in a mixture of 1 ml of water, 0.3 ml of methanol and 0.5 ml of a 4N hydrobromic acid solution, 12 ml of isopropanol was added slowly. After standing overnight 370 mg of the title compound was obtained by centrifugation, washing with acetone and drying.

IR (KBr-disc, values in cm$^{-1}$): 1805, 1785, 1645, 1620, 1595, 1472, 1417, 1350, 1295, 1285, 1146, 1058, 820 and 800.

PMR (360 MHz; D$_2$O; δ-values in ppm): 2.18 (m, 2H); 3.11 (t, 2H; J about 7.5 Hz); 3.21 (t, 2H; J about 7.5 Hz); 3.47 and 3.65 (2xd, 2H; J=18 Hz); 5.23 (s, 2H); 5.58 and 5.65 (2xd, 2H; J=13.2 Hz); 7.92 (t, 1H); 8.43 (d, 1H; J about 9 Hz).

EXAMPLE XXV

Preparation of
7β-ammonio-4-carboxylate-3-[(quinuclidin-1-ylio)-methyl]-3-cephem bromide from
3-bromomethyl-4-carboxy-7β-isopropylideneammonio-3-cephem bromide A mixture of 525 mg (purity 85%, 0.95 mmole) of 3-bromomethyl-4-carboxy-7β-isopropylideneammonio-3-cephem bromide, 2 ml (8 mmoles) of N,O-bis(trimethylsilyl)acetamide and 10 ml of 1,1,2-trichlorotrifluoroethane was stirred under nitrogen for 45 minutes at 0° C. With continuous stirring and maintaining the temperature at 0° C. 266 mg (2.4 mmoles) of quinuclidine in 10 ml of 1,1,2-trichlorotrifluoroethane was added over a period of 2 hours. After stirring for another hour 5 ml of isopropanol, 1 ml of methanol and 4 ml of a 1N hydrochloric acid solution was added with vigorous stirring and furthermore a small amount of water until a clear solution was obtained. After separation of the layers and extracting the organic layer with 2 ml of water the combined water layers were concentrated in vacuo until the volume of the reaction mixture was about 2 ml. Adding slowly 12 ml of isopropanol, filtering off the crystalline precipitate formed, washing and drying yielded 384 mg of the title product with a purity of 89%. The yield was 87%.

IR (KBr-disc, values in cm$^{-1}$): 3120, 2940, 2885, 2130, 1790, 1620, 1600, 1492, 1466, 1415, 1400, 1390, 1380, 1345, 1290, 1195, 1142, 1075, 935, 729 and 452.

PMR (360 MHz; D$_2$O; δ-values in ppm, determined in the presence of maleic acid): 1.7 (m, 6H); 1.9 (m, 1H); 3.2–3.4 (m, 6H); 3.49 and 3.61 (2xd, 2H; J about 17 Hz); 3.95 and 4.40 (2xd, 2H; J about 14 Hz); 4.98 (d, 1H; J=4.5 Hz); 5.23 (d, 1H; J=4.5 Hz).

EXAMPLE XXVI

Preparation of 3-bromo/chloromethyl-4-carboxy-7β-isobutylideneammonio-3-cephem chloride from 7β-phenylacetamido-3-methyl-3-cephem-4-carboxylic acid 1β-oxide After treating 373 g of a solution obtained as described in example Ia containing a mixture of bromo cephem silyl esters with 3.75 ml (13.9 mmoles) of tributyl phosphite at −37° C. for one hour the reduction of the sulphoxide was carried out with 4.1 ml (31.4 mmoles) of cyclooctene, 0.5 ml (3.9 mmoles) of N,N-dimethylaniline, 0.8 ml (10.4 mmoles) of N,N-dimethylformamide and 7.5 g (36.0 mmoles) of phosphorus pentachloride at −50° C. for 50 minutes. After adding 7.7 ml (60.7 mmoles) of N,N-dimethylaniline and 7.5 g (36.0 mmoles) of phosphorus pentachloride and stirring for 195 minutes at −50° C. a mixture of 30 ml (0.32 mmol) of isobutanol and 125 ml (1.39 mmol) of ethyl methyl ketone was added. Stirring was continued for 30 minutes without cooling and the reaction mixture was kept at 0° C. for 72 hours. Thus the precipitate formed was filtered off and dried in vacuo yielding 7.48 g of a mixture of the title compounds. The ratio of the bromo compound to the chloro compound was 2:1. The overall yield starting from 7β-phenylacetamido-3-methyl-3-cephem-4-carboxylic acid 1β-oxide amounted to 33%.

PMR-spectrum of the bromomethyl compound (360 MHz; CF$_3$CO$_2$D; δ-values in ppm): 1.22 (t, 3H); 2.53 (s, 3H); 2.89 (m, 2H); 4.28 and 4.34 (2xd, 2H; J=10.8 Hz); 5.34 (d, 1H; J=4.5 Hz); 5.81 (d, 1H; J=4.5 Hz).

PMR-spectrum of the chloromethyl compound (ibidem): 1.22 (t, 3H); 2.53 (s, 3H); 2.89 (m, 2H); 4.42 (s, 2H); 5.34 (d, 1H; J=4.5 Hz); 5.83 (d, 1H; J=4.5 Hz).

EXAMPLE XXVII

Preparation of 3-bromo/chloromethyl-4-carboxy-7β-cyclopentylideneammonio-3-cephem chloride from 7β-phenylacetamido-3-methyl-3-cephem-4-carboxylic acid 1β-oxide 706 g of a stock-solution obtained as described in example Ia containing a mixture of bromo cephem silyl esters were treated with 7.1 ml (26.2 mmoles) of tributyl phosphite and subsequently with 7.7 ml (59.1 mmoles) of cyclooctene, 1 ml (7.9 mmoles) of N,N-dimethylaniline, 1.5 ml (19.5 mmoles) of N,N-dimethylformamide and 14.3 g (68.7 mmoles) of phosphorus pentachloride in the usual way. Then 14.65 ml (115.5 mmoles) of N,N-dimethylformamide and 14.3 g of phosphorus pentachloride were added and stirring was continued at −50° C. for 210 minutes at −50° C. Then the reaction mixture was cooled down to −70° C. and a mixture of 55 ml (592 mmoles) of isobutanol and 25 ml (282 mmoles) of cyclopentanone was added. After stirring for 30 minutes at −40° C. followed by standing for 30 hours at −25° C. another 100 ml (1.13 mmol) of cyclopentanone were added and the temperature was allowed to rise to 28° C. After a further 4 hours at 2° C. the resultant precipitate was collected, washed with cyclopentanone and diethyl ether, and dried in vacuo to give 14.4 g of a mixture of the title compounds. The overall yield starting from 7β-phenylacetamido-3-methyl-3-cephem-4-carboxylic acid 1β-oxide amounted to 45%. The ratio of the bromo compound to the chloro compound was 3:1.

PMR-spectrum of the bromomethyl compound (360 MHz; CF$_3$COOD; δ-values in ppm): 1.96 (m, 4H); 2.95 (m, 4H); 4.30 (s, 2H); 5.30 (d, 1H; J=4.5 Hz); 5.70 (d, 1H; J=4.5 Hz).

PMR-spectrum (ibidem) of the chloromethyl compound: 1.96 (m, 4H); 2.95 (m, 4H); 4.39 (s, 2H); 5.30 (d, 1H; J=4.5 Hz); 5.72 (d, 2H; J=4.5 Hz).

EXAMPLE XXVIII

Preparation of 3-bromo/chloromethyl-4-carboxy-7β-cyclohexylideneammonio-3-cephem chloride from 7β-phenylacetamido-3-methyl-3-cephem-4-carboxylic acid 1β-oxide 455 g of a stock solution obtained as previously described in example Ia containing a mixture of bromo cephem silyl esters were treated with 4.4 ml (16.3 mmoles) of tributyl phosphite at −50° C. for 45 minutes. After adding 4.75 ml (36.4 mmoles) of cyclooctene, 0.65 ml (5.1 mmoles) of N,N-dimethylaniline, 0.9 ml (11.7 mmoles) of N,N-dimethylformamide and 8.8 g (42.3 mmoles) of phosphorus pentachloride stirring was continued at −50° C. for 45 minutes. Then 9.1 ml (71.8 mmoles) of N,N-dimethylaniline and 8.85 g (42.5 mmoles) of phosphorus pentachloride were added, the reaction mixture was stirred at −45° C. for 2 hours and a mixture of 34 ml of isobutanol and 20 ml (193 mmoles) of cyclohexanone was added, carefully maintaining the temperature below −50° C. After stirring for another 90 minutes at −50° C. the reaction mixture was kept overnight at 2° C. The resultant precipitate was filtered off, washed with acetonitrile and diethylether and dried in vacuo to give 11 g of a mixture of the title compounds. The ratio of the bromo compound to the chloro compound was 7:1. The overall yield starting from 7β-phenylacetamido-3-methyl-3-cephem-4-carboxylic acid 1β-oxide amounted to 48%.

PMR-spectrum (360 MHz; CF$_3$COOD; δ-values in ppm) of the bromomethyl compound: 1.64 (m, 2H); 1.93 (m, 4H); 2.79 (m, 4H); 4.27 and 4.34 (2xd, 2H; J=10.5 Hz); 5.34 (d, 1H; J=4.5 Hz); 5.88 (d, 1H; J=4.5 Hz).

PMR-spectrum (ibidem) of the chloromethyl compound: 1.64 (m, 2H); 1.93 (m, 4H); 2.79 (m, 4H); 4.39 and 4.45 (2xd, 2H; J=12.6 Hz); 5.34 (d, 1H; J=4.5 Hz); 5.91 (d, 1H; J=4.5 Hz).

EXAMPLE XXIX

Preparation of 3-bromo/chloromethyl-4-carboxy-7β-cyclohexylideneammonio-3-cephem bromide from 7β-phenylacetamido-3-methyl-3-cephem-4-carboxylic acid 1β-oxide 399 g of a stock solution obtained as previously described in example Ia containing a mixture of bromo cephem silyl esters were treated with 4.0 ml (14.8 mmoles) of tributyl phosphite at −50° C. for 50 minutes. After adding 4.3 ml (33.0 mmoles) of cyclooctene, 0.5 ml (3.9 mmoles) of N,N-dimethylaniline, 0.8 ml (10.4 mmoles) of N,N-dimethylformamide and 7.9 g (37.9 mmoles) of phosphorus pentachloride stirring was continued at about −47° C. for 40 minutes. Then 4.9 ml (38.7 mmoles) of N,N-dimethylaniline and 7.9 g (37.9 mmoles) of phosphorus pentachloride were added, the reaction mixture was stirred at −50° C. for 1 hour and 35 minutes and 60 ml (650 mmoles) of isobutanol was added. The temperature rised to −35° C. for just a moment, then the mixture was cooled again to −50° C. Then 20 ml of a solution of hydrogen bromide, 47% (174 mmoles HBr) and thereafter 50 ml (482 mmoles) of cyclohexanone were added. After stirring for another 2 hours at −50° C. the reaction mixture was kept for 6 days at 2° C. The resultant precipitate was filtered off, washed with cyclohexanone and acetone and dried in vacuo to give 9.9 g of a mixture of the title compounds. The ratio of the bromo compound to the chloro compound was 9:1. The overall yield starting from 7β-phenylacetamido-3-methyl-3-cephem-4-carboxylic acid 1β-oxide amounted to 46%.

IR-spectrum (KBr-disc; values in cm$^{-1}$): 1798, 1702, 1658, 1621, 1515, 1406, 1350, 1211, 1194, 1093, 1060, 996, 987, 702, 620.

NMR-spectrum (360 MHz; CF$_3$CO$_2$D; δ-values in ppm; int. ref. maleic acid; δ=6.35): 1.5–2.1 (m, 6H); 2.6–2.9 (m, 4H); 3.56 (s, 2H); 4.27, 4.33 (AB-q or d, 2H; J=10.5 Hz); 5.32 (d, 1H; J=4.5 Hz); 5.86 (d, 1H; J=4.5 Hz).

EXAMPLE XXX

Influence of the addition of a quaternary ammonium compound on the chloro/bromo ratio of the preparation of 4-carboxy-3-chloro/bromomethyl-7β-cyclohexylideneammonio-3-cephem chloride from 7β-phenlacetamido-3-methyl-3-cephem-4-carboxylic acid 1β-oxide 434.4 g of a stock solution obtained as previously described containing a mixture of bromo cephem silyl esters were treated with 4.2 ml (15.5 mmoles) of tributyl phosphite at −55° C. for 1 hour. The reduction of the sulphoxide moiety was carried out with 4.55 ml (34.9 mmoles) of cyclooctene, 0.6 ml (4.7 mmoles) of N,N-dimethylaniline, 0.9 ml (11.7 mmoles) of N,N-dimethylformamide and 8.4 g (40.3 mmoles) of phosphorus pentachloride in the usual way. After cooling the reaction mixture down to −66° C., stirring was continued and a mixture of 20 g (95.2 mmoles) of tetraethyl ammonium bromide, 32 ml of isobutanol, 25 ml of methylene chloride and 20 ml (193 mmoles) of cyclohexanone was added. After the reaction mixture was warmed up to 0° C. over 70 minutes, it was maintained at 2° C. overnight. The resultant precipitate was filtered off, washed with methylene chloride and dried to give 9.76 g of a mixture of the title compounds. The ratio of the bromo compound to the chloro compound was 2:3. The overall yield starting from 7β-phenylacetamido-3-methyl-3-cephem-4-carboxylic acid 1β-oxide amounted to 48%.

EXAMPLE XXXI

Preparation of 7β-amino-3-bromomethyl-3-cephem-4-carboxylic acid from 3-bromomethyl-4-carboxy-7β-isopropylideneammonio-3-cephem bromide In a centrifuge-tube, placed in an ultrasonic bath, 1000 mg (purity 79%, 90% bromo compound, 1.91 mmol) of 3-bromomethyl-4-carboxy-7β-isopropylideneammonio-3-cephem bromide were dissolved in 15 ml 2-methoxy ethanol. After adding 1.0 ml of a 2N hydrogen bromide solution this mixture was shaken and stirred during 10–15 minutes and the solution became clear. Stirring and shaking a solution of 0.60 ml (4.73 mmoles) of N,N-dimethylaniline in 15 ml acetonitrile was dropped to the mixture.

The precipitate was centrifugated and washed with 25 ml 80% acetonitrile, acetonitrile and ether, respectively. After drying in a nitrogen stream and then in vacuo the yield of 7β-amino-3-bromomethyl-3-cephem-4-carboxylic acid was 647.6 mg with a purity of 82.7%. The overall yield was 95.5%.

IR (KBr-disc, values in cm$^{-1}$): 3445, 3180, 1800, 1616, about 1535, 1410, 1350, 1290, 1210, 1150, 1114, 1059, 1001, 800, 791, 519, 432.

EXAMPLE XXXII

Preparation of 7β-amino-3-chloromethyl-3-cephem-4-carboxylic acid from 4-carboxy-3-chloromethyl-7β-isopropylideneammonio-3-cephem chloride In a centrifuge-tube, placed in an ultrasonic bath, 400 mg (purity 93.9%, 1.15 mmol) of 7β-isopropylideneammonio-4-carboxy-3-chloromethyl-3-cephem chloride were dissolved in 10 ml 2-methoxyethanol. After adding 1.5 ml of 2N hydrogen chloride and shaking and trilling during about 25 minutes a clear solution was obtained. During half an hour 0.45 ml (3.55 mmoles) of N,N-dimethylaniline dissolved in 15 ml acetonitrile was dropped to the mixture.

The precipitate was centrifugated and washed with 25 ml 80% acetonitrile, acetonitrile and ether, respectively. After drying in a nitrogen stream and then in vacuo the yield of 7β-amino-3-chloromethyl-3-cephem-4-carboxylic acid was 207.7 mg with a purity of 95.3%. The overall yield was 68.9%.

IR (KBr-disc, values in cm$^{-1}$): about 3440, 3180, 1804, 1622, about 1540, 1412, 1351, 1293, 1257, 1123, 1061, 51010, 889, 802, 792, 521, 430.

PMR (CF$_3$COOD, δ-values in ppm, 360 Mc, int. ref. TMS): 3.52, 4.40, 4.43 (2H; 2xd, J=11.9 Hz), 5.13, 5.15 (2H; 2xd, J=4.5 Hz).

EXAMPLE XXXIII

Preparation of
7β-ammonio-3-chloro/bromomethyl-3-cephem-4-carboxylate from
3-bromo/chloromethyl-4-carboxy-7β-isopropylideneammonio-3-cephem chloride A solution of 5 g (9.49 mmoles) of 3-chloro/-bromomethyl-4-carboxy-7β-isopropylideneammonio-3-cephem chloride (bromomethyl: chloromethyl=45:2-6) in 75 ml 2-methoxyethanol and 25 ml of dry acetone was treated with charcoal. After washing with 25 ml of acetone, slowly 30 ml of a mixture of 11.8 mmoles of N,N-dimethylaniline in acetone were dropped into the filtrate. After stirring for ten minutes the precipitate was filtered and washed with acetone and ether respectively. The yield after drying in vacuo was 2.16 g of 7β-ammonio-3-chloro/bromomethyl-3-cephem-4-carboxylate (57.0% 3-chloromethyl, 20.7% 3-bromomethyl as was found by spectroscopic means). The overall yield was 70%.

IR (KBr-disc, values in cm$^{-1}$): about 3420, 1800, 1621, about 1545, 1410, 1348, 1056, 1006, 799, 790.

EXAMPLE XXXIV

Preparation of
3-bromo/chloromethyl-4-carboxy-7β-isopopropylideneammonio-3-cephem bromide from
7β-ammonio-3-bromo/chloromethyl-3-cephem-4-carboxylate 6.585 g 7β-ammonio-3-bromo/chloromethyl-3-cephem-4carboxylate (bromomethyl:chloromethyl=31:69) were dissolved in 50 ml concentrated hydrogen bromide and 20 ml water. This mixture was stirred for five minutes whereafter 100 ml acetone was slowly added during half an hour. After stirring for one hour, 650 ml of acetone were added.

After four days standing in the refrigerator the precipitate was filtered and washed with acetone and ether. The yield after drying in vacuo was 8.032 g of 3-bromo/chloromethyl-4-carboxy-7β-isopropylideneammonio-3-cephem bromide (36% 3-bromomethyl, 64% 3-chloromethyl as was found by spectroscopic means).

EXAMPLE XXXV

Preparation of
3-chloromethyl-4-carboxy-7β-cyclopentylideneammonio-3-cephem chloride from
7β-ammonio-3-bromo/chloromethyl-3-cephem-4-carboxylate In a centrifuge-tube a small amount of 7β-ammonio-3-bromo/chloromethyl-3-cephem-4-carboxylate was dissolved in a small amount of a solution of concentrated hydrogen chloride. An excess of cyclopentanone was added to the solution.

After standing for a week-end in the refrigerator the product was washed with cyclopentanone and ether, respectively, filtered off and dried in vacuo giving 3-chloromethyl-4-carboxy-7β-cyclopentylideneammonio-3-cephem chloride as confirmed by NMR.

IR (KBr-disc, values in cm$^{-1}$): about 3410, 1795, 1706, 1681, 1633, 1506, 1405, 1353, 1098, 1061, 791, 691.

EXAMPLE XXXVI

Preparation of
chloro/bromomethyl-4-carboxy-7β-cyclohexylideneammonio-3-cephem chloride from
7β-ammonio-3-chloro/bromomethyl-3-cephem-4-carboxylate 200 mg of 7β-ammonio-3-chloro/bromomethyl-3-cephem-4-carboxylate (prepared in example XXXII) were dissolved in 1 ml of a solution of concentrated hydrogen chloride. Then 0.5 ml of cyclohexanone was added. After a short time a crystalline precipitate was formed. After stirring for 20 minutes cyclohexanone (1 ml) was added again, whereafter there was stirred for another 20 minutes. Then 4 ml of cyclohexanone was added slowly. After stirring for 10 minutes the product was filtered and washed with cyclohexanone and ether, respectively.

After drying in vacuo the yield was 235.2 mg of 3-chloro/bromomethyl-4-carboxy-7β-cyclohexylideneammonio-3-cephem chloride (80% 3-chloromethyl, 20% 3-bromomethyl as was found with NMR).

IR (KBr-disc, values in cm$^{-1}$): about 3410, 1800, 1706, 1664, 1630, 1526, 1410, 1351, 1187, 1098, 1061, 706, 692.

EXAMPLE XXXVII

Preparation of
chloro/bromomethyl-4-carboxy-7β-cycloheptylideneammonio-3-cephem chloride from
7β-ammonio-3-chloro/bromomethyl-3-cephem-4-carboxylate In a centrifuge-tube a small amount of 7β-ammonio-3-chloro/bromomethyl-3-cephem-4-carboxylate (prepared in example XXXIII) was dissolved in a small amount of a solution of concentrated hydrogen chloride. To the solution thus obtained an excess of cycloheptanone was added. After about one hour a very fine precipitate was formed. Warming the mixture and cooling down again, the mixture was made somewhat more granulated. The precipitate was centrifugated and washed with cycloheptanone and twice with ether, respectively.

After drying in vacuo crystalline 3-chloro/-bromomethyl-4-carboxy-7β-cycloheptylideneammonio-3-cephem chloride (93% 3-chloromethyl, 7% 3-bromomethyl as was found with NMR) was formed.

IR (KBr-disc, values in cm$^{-1}$): about 3410, 1798, 1710, 1643, 1522, 1405, 1358, 1098, 1061, 685.

EXAMPLE XXXVIII

Preparation of
3-bromo/chloromethyl-4-carboxy-7β-isobutylideneammonio-3-cephem chloride from
3-bromo/chloromethyl-4-carboxy-7β-isopropylideneammonio-3-cephem chloride In a centrifuge-tube a small amount of 3-bromo/-chloromethyl-4-carboxy-7β-isopropylideneammonio-3-cephem chloride was dissolved in a small amount of concentrated hydrogen chloride: An excess of ethyl methyl ketone was added. No precipitate was formed.

After standing for a week-end in the refrigerator the formed, white precipitate was filtered and washed with ethyl methyl ketone and ether, respectively. After drying crystalline 3-bromo/chloromethyl-4-carboxy-7β- secbutylideneammonio-3-cephem chloride was obtained.

IR (KBr-disc, values in cm$^{-1}$): about 3410, 1801, 1708, 1656, 1629, 1516, 1405, 1348, 1232, 1183, 1095, 1062, 1000, 708, 689.

EXAMPLE XXXIX

Preparation of 3-bromo/chloromethyl-4-carboxy-7β-cyclopentylideneammonio-3-cephem chloride from 3-bromo/chloromethyl-4-carboxy-7β-isopropylideneammonio-3-cephem chloride In a centrifuge-tube a small amount of 3-bromo/chloromethyl-4-carboxy-7β-isopropylideneammonio-3-cephem chloride was dissolved in a small amount of concentrated hydrogen chloride. Cyclopentanone was added to the solution. After standing for three hours the precipitate formed was filtered and washed with a little cyclopentanone and with ether, giving white crystalline 3-bromo/chloromethyl-4-carboxy-7β-cyclopentylideneammonio-3-cephem chloride.

IR (KBr-disc, values in cm$^{-1}$): about 3400, 1795, 1701, 1680, 1630, 1501, 1403, 1350, 1094, 1059, 715, 688.

EXAMPLE XXXX

Preparation of 3-bromo/chloromethyl-4-carboxy-7β-cyclohexylideneammonio-3-cephem chloride from 3-bromo/chloromethyl-4-carboxy-7β-isopropylideneammonio-3-cephem chloride In a centrifuge-tube a small amount of 3-bromo/chloromethyl-4-carboxy-7β-isopropylideneammonio-3-cephem chloride was dissolved in a 1:1 mixture of trifluoroacetic acid and concentrated hydrogen bromide.

Then about ¼ volume of cyclohexanone was added. The mixture was stirred and crystals were formed slowly. After standing for one hour the crystalline product was filtered and washed with ether.

After drying in vacuo crystalline 3-bromo/chloromethyl-4-carboxy-7β-cyclohexylideneammonio-3-cephem chloride was obtained.

IR (KBr-disc, values in cm$^{-}$): about 3410, 1798, 1710, 1656, 1620, 1512, about 1398, about 1342, 1220, 1180, 1090, 1058, 693, about 620.

EXAMPLE XX

Preparation of 3-bromo/chloromethyl-4-carboxy-7-cyclohexylideneammonio-3-cephem bromide from 3-bromo/chloromethyl-4-carboxy-7β-cyclopentylideneammonio-3-cephem chloride 7.5 g of 3-bromo/chloromethyl-4-carboxy-7β-cyclopentylideneammonio-3-cephem chloride were dissolved in 20 ml acetonitrile. 20 ml of concentrated hydrogen bromide (47%) were added and for some minutes the mixture was heated to about 55° C. After a clear solution has been obtained, the mixture was cooled down to 0° C. Then 10 ml of cyclohexanone was added. The mixture was red-brown and after a few minutes some crystals were formed.

After a night standing in the refrigerator the product was filtered, washed with acetonitrile and dried in vacuo. The yield of the creamy white crystalline 3-bromo/chloromethyl-4-carboxy-7β-cyclohexylideneammonio-3-cephem chloride was 6.68 g (purity 67.6% according to NMR-assay). The product contained also 11.6% 3-chloromethyl and some starting material as was found with NMR.

IR (KBr-disc, values in cm$^{-1}$): about 3410, 1799, 1710, 1655, 1620, 1512, about 1398, about 1340, 1220, 1180, 1089, 1057, 696, about 615.

PMR-spectrum of the bromomethyl compound (360 MHz, CF$_3$COOD, δ-values in ppm, int. ref. maleic acid, 25° C.): 1.64 (m, 2H); 1.93 (m, 4H); 2.79 (m, 4H); 4.27, 4.34 (AB-q, J=10.5 Hz, 2H); 5.34 (d, J=4.5 Hz, 1H); 5.88 (d, J=4.5 Hz, 1H).

PMR-spectrum (ibidem) of the chloromethyl compound: 1.64 (m, 2H); 1.93 (m, 4H); 2.79 (m, 4H); 4.39, 4.45 (AB-q, J=12.6 Hz, 2H); 5.34 (d, J=4.5 Hz, 1H); 5.91 (d, J=4.5 Hz, 1H).

EXAMPLE XXXXII

Preparation of 3-bromo/chloromethyl-4-carboxy-7β-cycloheptylideneammonio-3-cephem bromide from 3-bromo/chloromethyl-4-carboxy-7β-cyclopentylideneammonio-3-cephem chloride 75 mg of 3-bromo/chloromethyl-4-carboxy-7β-cyclopentylideneammonio-3-cephem chloride was dissolved in 0.2 ml acetonitrile. 0.2 ml of concentrated hydrogen bromide (47%) was added. This mixture was shortly heated till a clear solution was obtained. 0.1 ml of cycloheptanone was added to the yellow solution. Slowly, but faster than in example XXXIV crystals were formed. The solution was a little heated to accelerate the crystallisation.

After standing for a week-end in the refrigerator the product was filtered off and washed with acetonitrile and ether. After drying in a nitrogen-stream the yield was 61.0 mg of a white 3-bromo/chloromethyl-4-carboxy-7β-cycloheptylideneammonio-3-cephem bromide (purity 74.6% according to NMR-assay). The product contained also 11.7% of the 3-chloromethyl compound and and some starting material.

IR (KBr-disc, values in cm$^{-1}$): about 3405, 1795, 1710, 1638, about 1628, 1508, about 1395, 1340, 1217, 1088, 1056.

PMR-spectrum (360 MHz; CF$_3$COOD, δ-values in ppm, int. ref. maleic acid, 25° C.) of the bromomethyl compound: 1.56 (m, 4H); 1.81 (m, 4H); 3.02 (m, 4H), 4.27, 4.34 (AB-q, J=10.7 Hz, 2H); 5.35 (d, J=4.5 Hz, 1H); 5.80 (d, J=4.5 Hz, 1H).

PMR-spectrum (ibidem) of the chloromethyl compound: 1.56 (m, 4H); 1.81 (m, 4H); 3.02 (m, 4H); 4.39, 4.44 (AB-q, J=12.6 Hz, 2H); 5.35 (d, J=4.5 Hz, 1H); 5.83 (d, J=4.5 Hz, 1H).

EXAMPLE XXXXIII

Preparation of 3-bromo/chloromethyl-4-carboxy-7β-cyclopentylideneammonio-3-cephem bromide from 3-bromo/chloromethyl-4-carboxy-7β-cyclopentylideneammonio-3-cephem chloride 75 mg of 3-bromo/chloromethyl-4-carboxy-7β-cyclopentylideneammonio-3-cephem chloride were dissolved in 0.2 ml acetonitrile. 0.2 ml of concentrated hydrogen bromide (47%) was added. This mixture was shortly heated till everything was dissolved. The mixture was heated till clearness and very well stirred. The yellow solution was shaken in an ultra-sonic bath and became then somewhat turbid. Slowly some crystals were formed and 0.2 ml of acetonitrile and 0.2 ml of cyclopentanone were added.

After standing in the refrigerator for a week-end the product was filtered and washed with acetonitrile and ether. After drying in vacuo the yield was 38.9 mg of 3-bromo/chloromethyl-4-carboxy-7β-cyclopentylideneammonio-3-cephem bromide with a purity of 83.3%.

IR (KBr-disc, values in cm$^{-1}$): about 3400, 1791, 1705, 1673, 1622, 1491, 1392, 1342, 1217, 1089, 1056, 709, about 620.

PMR-spectrum (360 MHz; CF$_3$COOD, δ-values in ppm, 25° C., int. ref. maleic acid): 1.96 (m, 4H); 2.95 (m, 4H); 4.30 (s, 2H); 5.30 (d, J=4.5 Hz, 1H); 5.70 (d, J=4.5 Hz, 1H).

We claim:

1. A process for the preparation of 3-substituted methyl-3-cephem-4-carboxylic acid derivatives of formula I

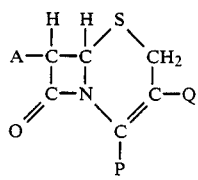

wherein
A is —NH$_2$,

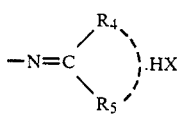

or —NH$_2$.HX,
P is —COOH; or —COO$\ominus$ when Q is —CH$_2$ $\oplus$R$_2$,
Q is —CH$_2$R$_1$ and A is NH$_2$; or Q is CH$_2$X and A is —NH$_2$, NH$_2$.HX or

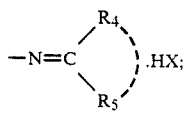

or Q is —CH$_2$ +R$_2$ and A is —NH$_2$; or Q is —CH$_2$ $\oplus$R$_2$.X$\ominus$ and A is —NH$_2$ or —NH$_2$.HX,
R$_1$ is (lower)alkoxy, (lower)alkylthio, (lower)alkanoyloxy, (lower)alkanoylthio or S—R$_3$ where R$_3$ is selected from the group consisting of pyridine, pyrimidine, pyridazine, pyrrole, imidazole, pyrazole, isoxazole, isothiazole, thiazole, triazole, oxadiazole, thiadiazole, triazine, thiatriazole and tetrazole linked by a ring carbon atom to the sulfur atom, unsubstituted or substituted on a ring carbon atom of a heterocyclid ring by lower alkyl, cyano, chloro, di(lower)alkylamino, (lower)alkoxy, (lower) alkoxycarbonyl, di(lower)alkylcarbamoyl, hydroxy, sulfo and carboxy, while ring nitrogen atoms of the heterocyclic thio group can have attached thereto a lower alkyl group, and attached to the first or the second carbon atom of a lower alkyl group attached to a carbon or a nitrogen atom of a heterocyclic ring di(lower)alkylamino, chloro, cyano, methoxy, (lower)alkyloxycarbonyl, N,N-dimethylcarbamoyl, hydroxy, carboxy and sulfo,
X is halogen or a mixture thereof when A is

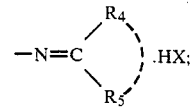

or X is bromo or chloro or a mixture thereof when A is —NH$_2$ or —NH$_2$.HX,
R$_2$ is a

group,
R$_4$ is alkyl of 1 to 8 carbon atoms,
R$_5$ is alkyl of 1 to 8 carbon atoms,
whereby R$_4$ and R$_5$ are the same or different or R$_4$ and R$_5$ together with the carbon atom to which they are attached form cycloalkylidene of 3 to 8 carbon atoms; starting from 3-methyl-3-cephem-4-carboxylic acid 1β-oxide derivatives of the formula II

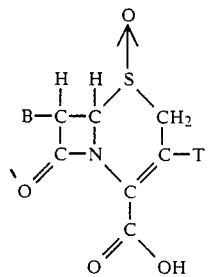

wherein
B is

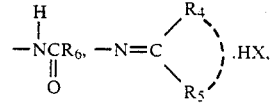

—NH$_2$ or —NH$_2$.HX,
T is —CH$_3$ when B is

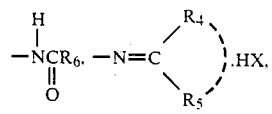

or T is —CH$_2$X when X is halogen or a mixture thereof when B is

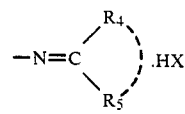

or X is bromo or chloro or a mixture thereof when B is —NH$_2$ or —NH$_2$.HX,
R$_4$ and R$_5$ are as defined above,
R$_6$ is —CH$_2$R$_7$ wherein R$_7$ is hydrogen, aryl, alkyl, cycloalkyl, alkenyl, aryloxy, alkyloxy, arylthio, alkylthio, or R$_6$ is an aryl group; characterized by carrying out subsequently the following reactions without isolation of the intermediate products: when A is —NH₂, Q is —CH₂R₁, or CH₂ ⊕R₂ or —CH₂—⊕R₂X⊖, and P, R₁₋₃ and X are as described above, and B is

and T, R₆ and R₇ are as defined above:
(a) silylation of the carboxy group
(b) light-induced bromination of the 3-methyl group of a compound of formula II to obtain the corresponding 3-bromomethyl compound using a N-bromo-amide or a N-bromo-imide as brominating agent,
(c) replacement of any bromine introduced in step (b) in the methylene group adjacent to the sulfur atom in the dihydrothiazine ring by hydrogen by reaction with a trialkyl or triaryl phosphite,
(d) deoxygenation of the sulfoxy group by reaction with phosphorus pentachloride in the presence of an olefinic compound having at least one carbon-carbon double bond with no more than two hydrogen atoms attached thereto in the presence or absence of added or already present catalyst or additive,
(e) an imide chloride forming reaction splitting the 7β-acylamino substituent by adding sequentially N,N-dimethylaniline or other suitable tertiary amine and phosphorus pentachloride,
(f) a reaction of the imide chloride with an alcohol to form the corresponding imino ether and/or the 7-amino-cephem derivatives,
(f') addition or not of sodium iodide,
(f'') formation or not of a 7β-(cyclo) alkylidene-imino/ammonio derivative by adding a ketone and
(g) introduction of R₁ or R₂ by replacement of the bromine in the 3-bromomethyl group, introduced in step (b) water for hydrolysis of the ammonium group; when A is

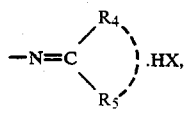

and P, Q, R₁₋₅ and X are as defined B above and B is

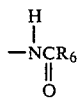

and T, R₆ and R₇ are as defined above:
by carrying out reactions a-f as described above, and adding a ketone R₄CO—R₅;
when A is —NH₂ or —NH₂.HX, Q is —CH₂X and P and X are as defined above, and B is

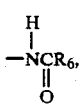

and T, R₆ and R₇ are as defined above:
by carrying out reactions a-f as described above, and if necessary, adding water for hydrolysis of the ammonio group; when A is

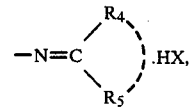

Q is —CH₂Br and P, X, R₄ and R₅ are as defined above, and B is

and T, R₆ and R₇ are as defined above:
by carrying out reactions a-f as described above, and adding a ketone R₄R₅CO in the presence of an acid other than HCl;
when A is

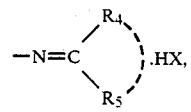

Q is —CH₂Cl and P, X, R₄ and R₅ are defined above and B is

and T, R₆ and R₇ are as defined above:
by carrying out reactions a-f as described above, and adding a ketone R₄R₅CO in the presence of hydrogen chloride or in the presence of a chloride providing agent together with a nitrogen containing base;
when A is —NH₂ or —NH₂.HX, Q is —CH₂R₁ or —CH₂−⊕R₂ or —CH₂ ⊕R₂X⊖ and P, R₁₋₃ and X are as defined above, and B is

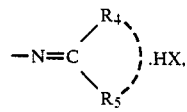

and T, R₄ and R₅ are as defined above:
introduction of R₁ or R₂ by replacement of halogen in the halomethyl group and, if necessary water for hydrolysis of the ammonio group; when A is

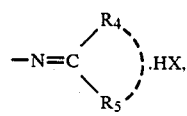

Q is —CH₂X, and P, X, R₄ and R₅ are as defined above, and B is

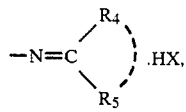

another one than being prepared or B is —NH$_2$.HX, and T, X, R$_4$ and R$_5$ are as defined above:

addition of a suitable ketone R$_4$R$_5$CO, corresponding with B; when A is —NH$_2$ or —NH$_2$.HX, Q is —CH$_2$X and P and X are as defined above, and B is

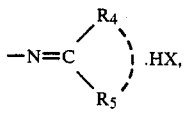

and T, X, R$_4$ and R$_5$ are as defined above:

water for hydrolysis of the ammonio group.

2. A process according to claim 1, characterized by the preparation and isolation of compounds of formula I from compounds of formula II wherein
Q is —CH$_2$R$_1$,
R$_1$ is
(1-sulfomethyl-tetrazol-5-yl)thio,
(1-methyl-tetrazol-5-yl)thio,
(1,2,3-triazol-5-yl)thio,
(1-carboxymethyl-tetrazol-5-yl)thio,
(1-(2-dimethylamino)ethyl-tetrazol-5-yl)thio,
(5-methyl-1,3,4-thiadiazol-2-yl)thio,
and A, P and X are as defined in claim 1, and B is

and T, R$_6$ and R$_7$ are as defined in claim 1;
A is

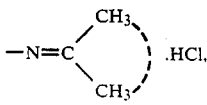

Q=—CH$_2$X where X is bromo or chloro, and P is defined as in claim 1, and B is

and T, R$_6$ and R$_7$ are as defined in claim 1;
A is —NH$_2$ or —NH$_2$.HCl, Q is —CH$_2$X where X is bromo or chloro or a mixture thereof, and P is as defined in claim 1, and B is

and R$_6$, R$_7$ and T are as defined in claim 1;
Q is —CH$_2$R$_1$ or —CH$_2$ ⊕R$_2$ or —CH$_2$ ⊕R$_2$X⊖
where
R$_1$ is
(1,2,3-triazol-5-yl)thio,
(1-methyl-tetrazol-5-yl)thio,
(5-methyl-1,3,4-thiadiazol-2-yl)thio,
(6-hydroxy-2-methyl-5-oxo-1,2,4-triazol-3-yl)-thio,
(1,3,4-thiadiazol-5-yl)thio,
R$_2$ is
(1-pyridinio),
(quinuclidinio-1-ylio),
(1-methylpyrrolidin-1-ylio),
(cyclopenta[b]pyridin-1-ylio),
and A, P and X are as defined in claim 1, and B is —NH$_2$, —NH$_2$.HX or

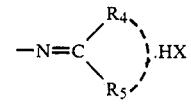

where R$_4$, R$_5$ is isopropylidene, cyclopentylidene or cyclohexylidene and T and X are as defined in claim 1;
A is

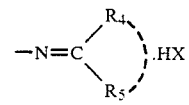

where
R$_4$,R$_5$ is isopropylidene,
R$_4$,R$_5$ is isobutylidene,
R$_4$,R$_5$ is cyclopentylidene,
R$_4$,R$_5$ is cyclohexylidene,
R$_4$,R$_5$ is cycloheptylidene,
and P and X are as defined in claim 1, and B is

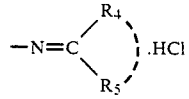

where R$_4$,R$_5$ is isopropylidene or cyclopentylidene, another one than being prepared, or B is —NH$_2$ or —NH$_2$.HX, and T and X are as defined in claim 1;
A is

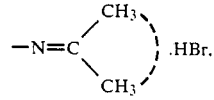

Q and P are as defined in claim 1, and B is —NH$_2$, and T is as defined in claim 1;
A is —NH$_2$, Q and P are as defined in claim 1, and B is

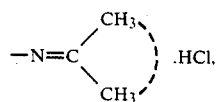

and T is as defined in claim 1.

* * * * *

UNITED STATES PATENT AND TRADEMARK OFFICE
CERTIFICATE OF CORRECTION

PATENT NO. : 4,921,954

DATED : May 1, 1990

INVENTOR(S) : HENDRIK A. WITKAMP; JAN VERWEIJ; JAN J. DeKONING; HERMAN H. GROOTVELD; and EVERARDUS J.A.M. LEENDERTS It is certified that error appears in the above-identified patent and that said Letters Patent is hereby corrected as shown below:

| Col. | Line | |
|---|---|---|
| 1 | 12 | "amino-and" should be -- amino- and -- |
| 37 | 4 | " $-CH_2-\oplus R_2 X\ominus$, " should be -- $-CH_2-\overset{\oplus}{R_2}X^{\ominus}$ -- |

Signed and Sealed this

Fourteenth Day of January, 1992

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,921,954

DATED : May 1, 1990

INVENTOR(S) : HENDRIK A. WITKAMP, JAN VERWEIJ, JAN J. DeKONING, HERMAN H. GROOTVELD, EVERARDUS J.A.M. LEENDERTS

It is certified that error appears in the above-identified patent and that said Letters Patent is hereby corrected as shown below:

| Col. | Line | |
|---|---|---|
| 1 | 12 | "amino-and" should read --amino- and--. |
| 4 | 18 | "and" between "X," and "$R_4$" should be deleted |
| 4 | 54 | "$R_1$" should read "$R_{1-3}$" |
| 5 | 46 | Left out and "B" is -- $-NCR_6-$ -- (with H above and O below) |
| 6 | 8&9 | "$-CH_2 \oplus R_2$" should read -- $-CH_2 {}^\oplus R_2$ -- |
| | | "$-CH_2 \oplus R_2 X\ominus$where" should read -- $-CH_2 {}^\oplus R_2 X^\ominus$ where-- |
| 6 | 15 | "cyclopenta[b]pyridin-1ylio" should read --cyclopenta[b]pyridin-1-ylio-- |
| 6 | 60 | "$-NH_2$and" should read -- $-NH_2$ and-- |
| 10 | 55 | "intermediate" should read --intermediates-- |
| 11 | 5 | "bromo-or" should read --bromo- or-- |
| 11 | 16 | "ammonio-e-bromo" should read --ammonio-3-bromo-- |
| 35 | 47/48 | "$-CH_2 \oplus R_2.X\ominus$" should read -- $-CH_2 {}^\oplus R_2.X^\ominus$ -- |
| 35 | 57 | "heterocyclid" should read --heterocyclic-- |

UNITED STATES PATENT AND TRADEMARK OFFICE
CERTIFICATE OF CORRECTION

PATENT NO. : 4,921,954

DATED : May 1, 1990

INVENTOR(S) : HENDRIK A. WITKAMP, JAN VERWELJ, JAN J. DeKONING, HERMAN H. GROOTVELD, EVERARDUS J.A.M. LEENDERTS

Page 2 of 2

It is certified that error appears in the above-identified patent and that said Letters Patent is hereby corrected as shown below:

| Col. | Line |  |
|------|------|--|
| 36 | 48-54 | Please delete "$-N=C\begin{subarray}{c}R_4\\ R_5\end{subarray}$ .HX" |
| 37 | 4 | "$-CH_2-\oplus R_2 X\ominus-$" should read -- $-CH_2{}^{\oplus}R_2 X^{\ominus}-$ -- |
| 38 | 48 | "$-CH_2\overset{\oplus}{-}R_2$" should read -- $-CH_2\overset{\oplus}{}R_2$ -- |

This certificate supersedes Certificate of Correction issued January 14, 1992.

Signed and Sealed this

Ninth Day of June, 1992

Attest:

DOUGLAS B. COMER

Attesting Officer

Acting Commissioner of Patents and Trademarks